United States Patent [19]
Majeed et al.

[11] Patent Number: 5,972,382
[45] Date of Patent: *Oct. 26, 1999

[54] USE OF PIPERINE AS A BIOAVAILABILITY ENHANCER

[75] Inventors: Muhammed Majeed; Vladimir Badmaev, both of Piscataway, N.J.; R. Rajendran, Bangalore, India

[73] Assignee: Sabinsa Corporation, Piscataway, N.J.

[*] Notice: This patent is subject to a terminal disclaimer.

[21] Appl. No.: 09/005,594

[22] Filed: Jan. 12, 1998

Related U.S. Application Data

[60] Division of application No. 08/550,496, Oct. 30, 1995, Pat. No. 5,744,161, which is a continuation-in-part of application No. 08/393,738, Feb. 24, 1995, Pat. No. 5,536,506.

[51] Int. Cl.$^6$ .............................. A61F 2/02; A61F 6/06; A61K 9/70; A61K 9/48
[52] U.S. Cl. .................. 424/464; 424/195.1; 424/423; 424/430; 424/434; 424/443; 424/451
[58] Field of Search .................. 424/464, 195.1, 424/423, 430, 434, 443, 451

[56] References Cited

U.S. PATENT DOCUMENTS

| | | | |
|---|---|---|---|
| 4,284,657 | 8/1981 | Stanton | 426/651 |
| 5,744,161 | 4/1998 | Majeed et al. | 424/464 |

*Primary Examiner*—Carlos A. Azpuru
*Attorney, Agent, or Firm*—Nikaido Marmelstein Murray & Oram, LLP

[57] ABSTRACT

Compositions and methods for the improvement of gastrointestinal absorption and systemic utilization of nutrients and nutritional supplements, wherein the compositions comprise a minimum of 98% of pure alkaloid piperine. The method comprises oral, topical, or parenteral administration of the compositions of the invention. A new process for the extraction and purification of piperine is also disclosed.

60 Claims, 3 Drawing Sheets

USE OF PIPERINE AS A BIOAVAILABILITY ENHANCER

This application is a divisional application of U.S. patent application Ser. No. 08/550,496, filed on Oct. 30, 1995, now issued as U.S. Pat. No. 5,744,161, which is a continuation-in-part of U.S. patent application Ser. No. 08/393,738, filed on Feb. 24, 1995, now issued as U.S. Pat. No. 5,536,506.

BACKGROUND OF THE INVENTION

1. Field of the Invention

The present invention relates to a method for enhancing the bioavailability of nutritional compounds. The present invention also relates to compositions for such enhancement.

The fifty percent increase in life expectancy of Americans from 1930 to 1980 can, in part, be attributed to the improvement in nutrition in the United States during that period. However, the situation today remains far from ideal, since six out of ten of the leading causes of death in this county, including heart attack, cancer, cirrhosis of the liver, and diabetes, are linked to diet. It becomes increasingly obvious that many of those diseases could be prevented with a well balanced diet and efficient nutritional supplementation with certain vitamins and minerals.

The problem is particularly severe in older Americans. Approximately 30 percent of older Americans do not get the dietary requirements of all the essential nutrients. The hazards of food-drug interactions in depleting essential nutrients are well recognized. It is unavoidable that old age calls for increased use of medications. For example, use of certain antibiotics decreases absorption of calcium and iron, while EDTA chelation therapy decreases absorption of zinc, iron, copper, and magnesium.

In addition, many foods which increase the risk of cancer and cardiovascular disease have to be eliminated from the diet, which further depletes the sources of essential nutrients. For example, excellent sources of vitamin B and vitamin D, such as red meat, liver, egg yolk, cheese and dairy products, are often limited because of their high cholesterol content.

Limited menu also causes a depletion of essential amino acids, such as tryptophan, which is important precursor of neurotransmitters, and may play a role in the prevention of brain deterioration with aging.

The availability of essential nutrients is further compromised by poor gastrointestinal absorption.

The traditional way to offset insufficient nutrient supplementation, insufficient gastrointestinal absorption and insufficient metabolic utilization of essential nutrients is to administer large doses of compensating materials, such as vitamin and mineral supplements.

The present invention provides an alternative method for improving nutritional status by increasing the bioavailability of various nutritional materials.

The bioavailability of nutrients is also relevant to animal health as well as human health. Thus, the compositions and methods of the invention are also intended to be used in veterinary practice.

2. Description of Related Art

Documents describing ayurvedic medicine dating from the period between the seventh century B.C. and the sixth century A.D. describe "trikatu". Trikatu is a Sanskrit word meaning three acrids, and refers to a combination of black pepper (*Piper nigrum Linn.*), long pepper (*Piper longum Linn.*) and ginger (*Zingiber officinale Rosc.*). In traditional ayurvedic medicine these drugs are essential ingredients of many prescriptions and formulations used for a wide range of diseases. Experimental evidence shows that the use of "trikatu", and its constituents individually as well as collectively, enhances the bioavailability of a number of drugs. In those studies carried out in animals as well as human volunteers, it was noted that the active component responsible for the increase in bioavailability of various drugs was piperine.

Piperine, or mixtures containing piperine, have been shown to increase the bioavailability, blood levels and efficacy of a number of drugs including ingredients of vasaka leaves (Bose, K. G., (1928) Pharmacopeia India, Bose Laboratories, Calcutta), vasicine (Atal et al., *Journal of Ethnopharmacology*, 4, 229–233 (1981)), sparteine (Atal et al., ibid), sulfadiazine (Atal et al., ibid), rifampicin (Zutshi, U. et al. (1984) *Journal of the Association of Physicians of India*, 33, 223–224), phenytoin (Bano et al., Planta Medica, 1987, pp. 568–569), pentobarbitone (Majumdar, A. N. et al. (1990), *Indian Journal of Experimental Biology*, 28, 486–487), theophylline (Bano et al., *Eur. J. Clin. Pharmacol.* (1991) 41:615–617) and propranolol (ibid).

The effect of piperine on the bioavailability of propranolol has been studied. The chronic oral administration of the anti-hypertensive agent propranolol is frequently rendered difficult due to the fact that steady therapeutic levels of this drug are not achieved or maintained. In addition, large doses are needed to be administered for efficacy and this frequently causes side-effects. Piperine has been shown to enhance the bioavailability of this drug. Propranolol administered with piperine shows a significant increase in plasma levels of the drug, presumably due to decrease in metabolism by the liver.

Similar results have been obtained with piperine and vasicine, theophylline, and phenytoin. Piperine has also been added in multi-drug formulations for the treatment of tuberculosis and leprosy. A formulation containing rifampicin, pyrazinamide and isoniazid has been tested in human volunteers (Indian Patent No. 1232/DEL/89). For most drugs, the comparative levels and peak concentration of the drugs in the presence of piperine were higher. The applicability of these results to the development of anti-tuberculosis and anti-leprosy formulations, which are presently cost prohibitive in developing countries, is apparent. Bioavailability enhancement helps to lower dosage levels and shorten the treatment course.

In summary, all of these examples clearly illustrate the role of piperine as a drug bioavailability enhancer. The combination of piperine with tested drugs is effective primarily due to higher plasma concentration and a longer stay of the drugs in the body. The reduced dose of highly toxic drugs and their enhanced efficacy is obviously desirable.

The effective bioenhancing dose of piperine for drug compounds varies, but the prior art studies indicate that a dose of approximately 10% (wt/wt) of the active drug could be regarded as an appropriate bioenhancing dose for most drugs.

There are two plausible explanations of the role that piperine may have in drug bioavailability: a) non-specific mechanisms promoting rapid absorption of drugs and nutrients, e.g., increased blood supply to the gastrointestinal tract, decreased hydrochloric acid secretion which prevents breakdown of some drugs, increased emulsifying content of the gut, increased enzymes like gamma-glutamyl transpeptidase which participate in active and passive transport of nutrients to the intestinal cells, and b) non-specific mechanisms inhibiting enzymes participating in biotransformation of drugs, preventing their inactivation and elimination. See: Annamalai, A. R., Manavalan, R. (1990) Effects of 'Trikatu' and its individual components and piperine on gastrointestinal tracts: Trikatu—a bioavailable enhancer. *Ind. Drugs* 27(12); pp. 595–604; Johri, R. K. et al. (1992) Piperine-mediated changes in the permeability of rat intestinal epithelial cells. *Bioch. Pharmacol.* 43; pp. 1401–1407; Atal, C. K. et al. (1985) Biochemical basis of enhanced drug availability by piperine: Evidence that piperine is a potent inhibitor of drug metabolism. *J. Pharmacol. Exp. Therap.* 232; pp. 258–262; and Singh, J. et al. (1986) Piperine-mediated inhibition of glucuronidation activity in intestine: evidence that piperine lowers the endogenous UDP-glucuronic acid content. *J. Pharmacol. Exp. Therap.* 2236; pp.448–493.

Most drugs co-administered with piperine are probably more bioavailable as a result of both of the mechanisms, i.e., increased absorption from the gut and the slow down of biotransformation, inactivation and elimination from the system. The latter mechanism is probably the most important in sustaining the elevated blood levels of the drug, and making it more bioavailable to the tissue. Although a rapid absorption to the blood stream may account for increased blood levels of the drug, it is the inhibition of drug biotransforming enzymes with piperine that makes a drug stay in the body longer, in higher quantities, which makes it more effective.

Based on available literature data, it seems that piperine in a daily dose of at least 20 mg per person operates through inhibiting enzymes that would otherwise biotransform and speed up elimination of many drugs (Zutshi, U. et al. (1989) A process for the preparation of pharmaceutical combination with enhanced activity for treatment of tuberculosis and leprosy. Indian Patent No. 1231/Del/89; Zutshi et al. (1984) Influence of piperine on rifampicin blood levels in patients of pulmonary tuberculosis. *J. Assoc. Phys. Ind.* 33; pp. 223–224; Ban, C. K. et al. (1991) The effect of piperine on the bioavailability and pharmacokinetics of propranolol and theophylline in healthy volunteers. *European J. Clin. Pharm.* 41; pp. 615–618 and Bano, G. et al. (1978) The effect of piperine on the pharmacokinetics of phenytoin in healthy volunteers. *Planta Medica* 53; pp. 568–570).

Interestingly, the dose of piperine that inhibits the biotransforming enzymes operates regardless of whether it is administered concurrently with the drug. This point can be illustrated by experiments with theophylline and phenytoin, where 20 mg of piperine was administered for seven days prior to the administration of either drug [Ban, C. K. et al. (1991) The effect of piperine on the bioavailability and pharmacokinetics of propranolol and theophylline in healthy volunteers. *European J. Clin. Pharm.* 41; pp. 615–618 and Bano, G. et al. (1978) The effect of piperine on the pharmacokinetics of phenytoin in healthy volunteers. *Planta Medica* 53; pp. 568–570]. Since that regimen resulted in increased blood levels of the administered drugs, and dramatically prolonged the elimination time, the plausible explanation is that the prior administration of piperine inhibited drug biotransforming enzymes. In fact, this seems to be the only explanation for the increased bioavailability, since piperine administered separately from the drug could not possibly affect gastrointestinal events leading to its rapid absorption.

Another interesting observation is that doses of piperine below what is considered effective in inhibiting the biotransforming enzymes, may still be sufficient to enhance the rapid absorption of a drug from the gut. This phenomenon can be illustrated by the co-administration of piperine with the anti-hypertensive drug propranolol (Zutshi, U. et al. (1989) A process for the preparation of pharmaceutical combination with enhanced activity for treatment of tuberculosis and leprosy. Indian Patent No. 1231/Del/89).

Propranolol when administered with piperine showed a significant increase in blood levels. The maximum blood concentration of the drug increased two fold with piperine. Importantly, despite dramatically improving the bioavailability of propranolol, piperine, as used in a 3 mg dose, did not affect the elimination rate of the drug.

In an experimental design distinct from previous studies, the anti-asthmatic drug theophylline and the anti-epileptic drug phenytoin were tested (Ban, C. K. et al. (1991) The effect of piperine on the bioavailability and pharmacokinetics of propranolol and theophylline in healthy volunteers. *European J. Clin. Pharm.* 41; pp. 615–618 and Bano, G. et al. (1978) The effect of piperine on the pharmacokinetics of phenytoin in healthy volunteers. *Planta Medica* 53; pp. 568–570). The study was done on six healthy volunteers. The participants were pretreated with 20 mg of piperine daily for seven days before receiving 150 mg of theophylline or 300 mg of phenytoin.

The maximum concentration of theophylline was 1.5 times higher in subjects pretreated with piperine. Importantly, the elimination rate of the drug was significantly slowed down with piperine pretreatment.

Phenytoin blood concentration rose more rapidly in the group pretreated with piperine than in the group receiving the drug alone. The pretreated group attained maximum concentration of the drug in shorter time and in significantly higher concentrations. The pretreatment with piperine resulted in significantly slower elimination of the drug.

The prior art discussed above clearly illustrates the role of piperine as a bioavailability enhancer, and the importance of its effective dose on the overall mechanism of enhanced bioavailability.

In the case of propranolol, the co-administration with only 3 mg of piperine resulted in doubling its blood levels, but without slowing down the drug elimination rate. Thus, it may be inferred that, in a small dose, piperine may not inhibit the biotransforming enzymes or affect the elimination rate of a drug. Rather, it may operate through enhancement of gastrointestinal events leading to rapid absorption mechanisms.

SUMMARY OF THE INVENTION

The present invention is directed to preparations and methods of using such preparations to improve the bioavailability of nutritional compounds. The compositions and methods of the present invention increase gastrointestinal absorption, improve crossing over through certain biological barriers such as respiratory lining, urinary lining, blood brain barrier and skin, and systemic utilization of certain nutrients and biological compounds.

The compositions and methods of the present invention contain, as an essential ingredient, piperine. This compound may be obtained as an extract from the fruit of *piper nigrum* comprising at least 98% piperine. Alternatively, the compositions may be prepared from an extract of the fruit of *piper longum*. Piperine made synthetically may also be used in the present invention. Compositions of the present invention may also contain extract from roots of *zingiber officinale*, with the active ingredients 6-gingerol and 6-shogoal. The compositions may be formulated with the extract from fruit of *piper nigrum*, extract from fruit of *piper longum*, and extract from fruits of *zingiber officinale* combined in any weight ratio. Preferred weight ratios include 2:2:1, 1:1:1, 2:1:1, and 1:2:1.

As a daily supplement taken with a nutrient or nutrients by an average healthy adult, piperine is effective and safe in a broad dose range. A preferred effective dose range of piperine for oral use to enhance nutrient bioavailability is 0.0004–0.15 mg/kg/day. The recommended dose of piperine for a healthy individual for oral use is approximately 5 mg/person/day. The recommended dose in cases of clinically diagnosed nutritional deficiencies is up to 15 mg/person/day in divided doses, i.e., 5 mg every six hours (in the morning, at noon, and in the evening). When used as a preparation for topical or parenteral use to improve crossing over through a biological barrier, the compositions of the present invention contain, as an essential ingredient, 0.00004–0.015 mg/kg of body weight of piperine. The nutritional materials are used in nutritionally effective amounts.

Black pepper contains approximately 5–9% piperine and is listed by the FDA as an herb which is generally recognized as safe (GRAS) for its intended use as spice, seasoning, or flavoring. The bioenhancing dose of piperine as used in the present invention is a maximum of approximately 15 mg/person/day, or no more than 20 mg/day in divided doses, which corresponds to from several thousands to up to 40,000 times less than the $LD_{50}$ dose of piperine, as established in various experiments on rodents.

The active ingredient of the present invention may be prepared by a novel process which produces piperine of a purity greater than 98%.

DESCRIPTION OF THE PREFERRED EMBODIMENTS

Figure 1:
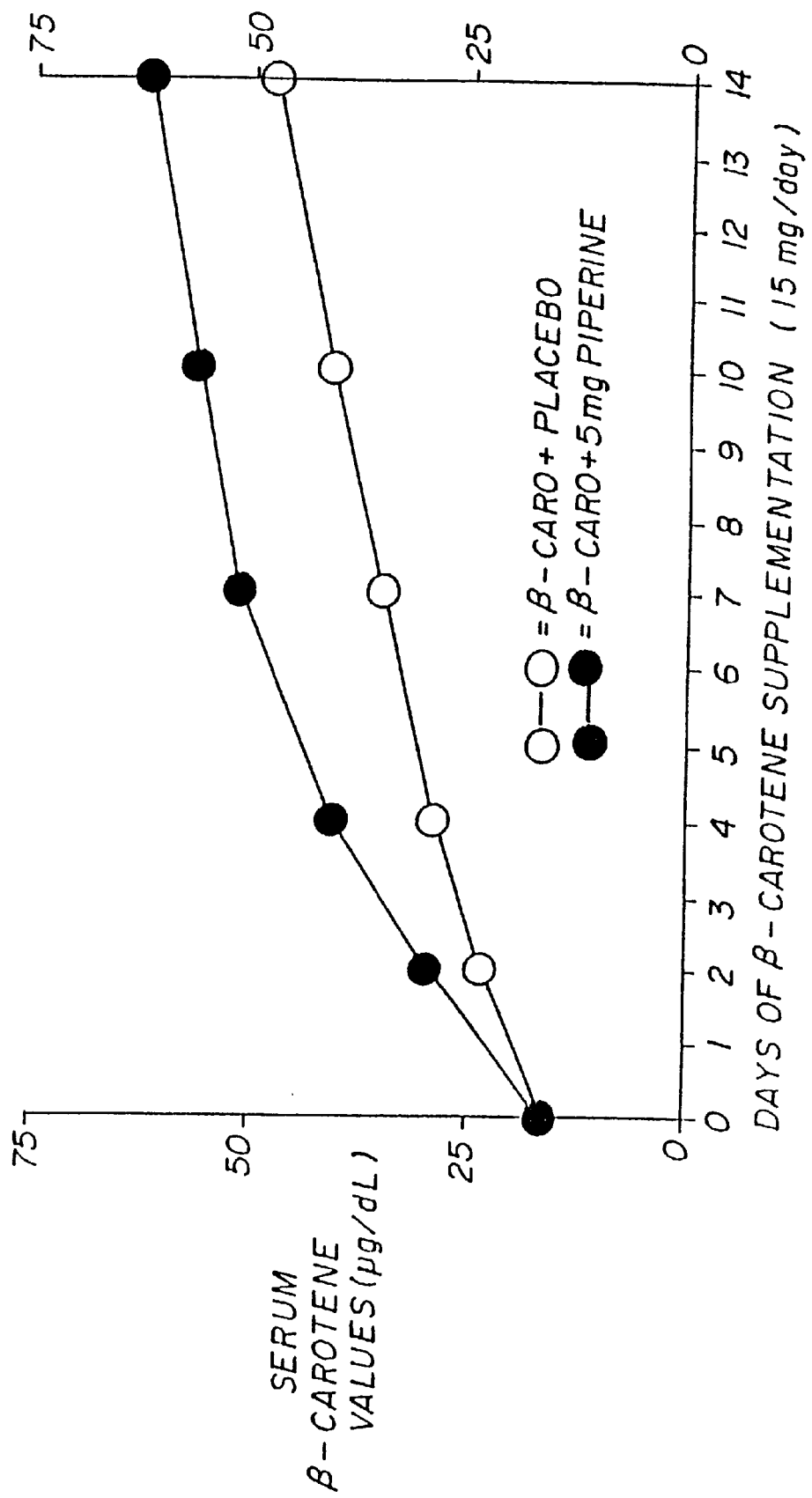
FIG. 1 shows the mean serum β-carotene changes during piperine trial.
Figure 2:
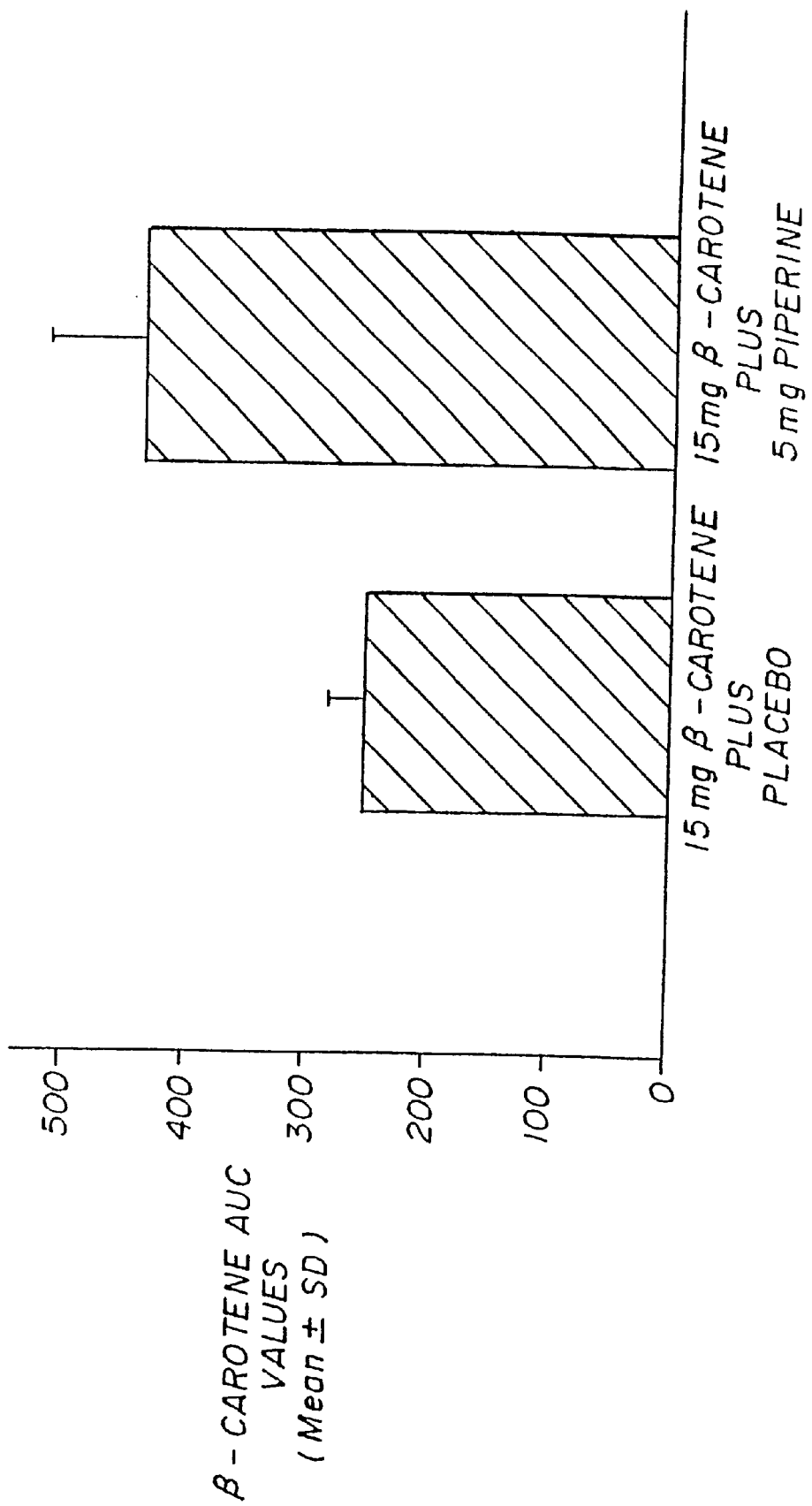
FIG. 2 shows AUC comparisons of β-carotene 14-day bioavailability.
Figure 3:
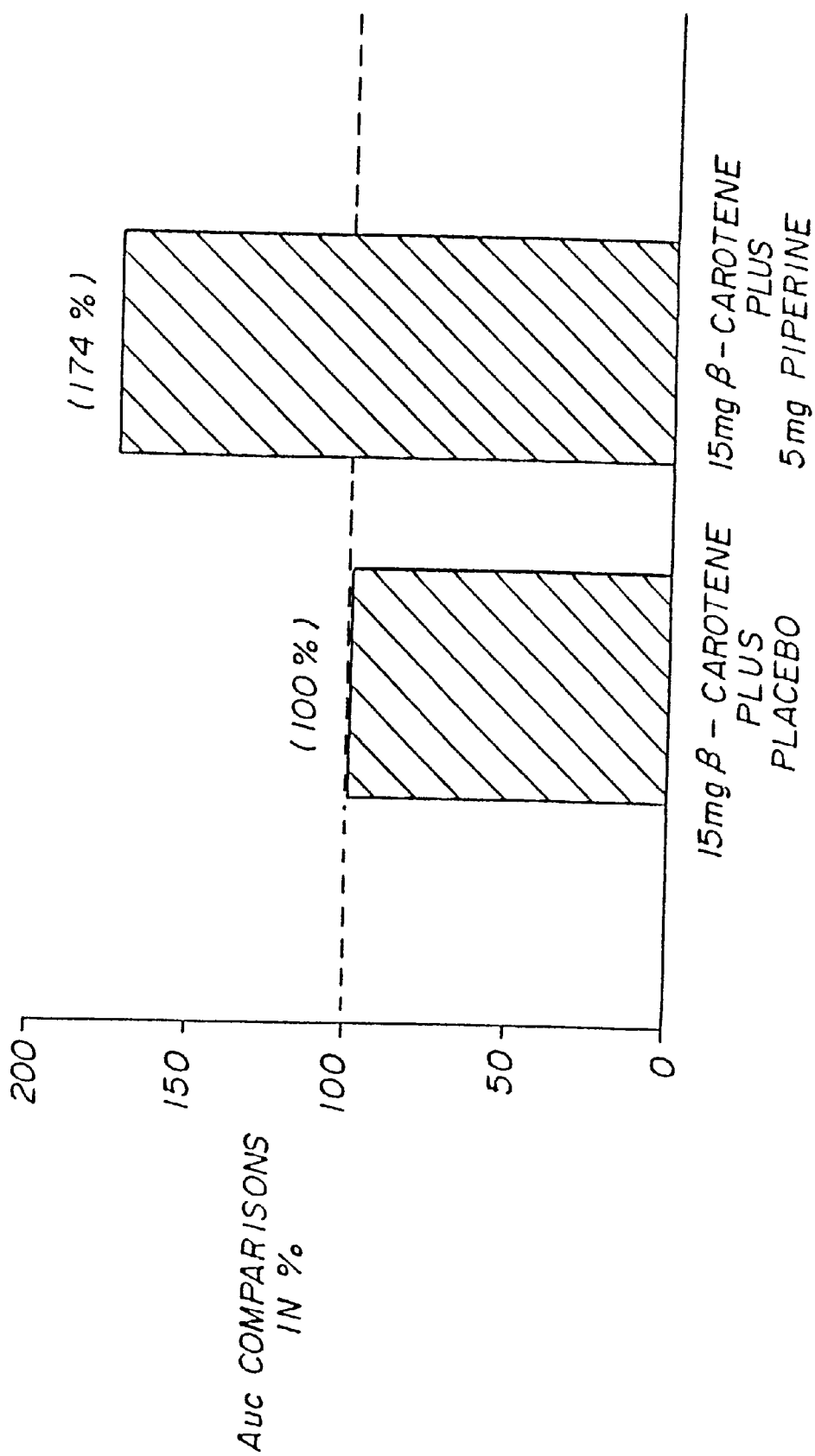
FIG. 3 shows Percentage comparison of β-carotene AUC data.

The present invention is directed to preparations and methods of using such preparations to improve the bioavailability of various nutritional compounds. The compositions and methods of the present invention increase gastrointestinal absorption, improve crossing over through certain biological barriers such as respiratory lining, urinary lining, blood brain barrier and skin, and systemic utilization of certain nutrients and biological compounds.

The compositions of the invention also act by increasing thermogenesis. This mechanism is believed to be triggered by activation of thermoreceptors and release of catecholamines and/or direct action as beta 1,2,3-adrenoceptor agonist. Secretion of catecholamines can also be mediated by ATP via a P2-type purinergic receptors, and through a direct or indirect stimulation by the compositions of the invention of dopaminergic and serotinergic systems.

It is known that stimulation of beta-3 adrenoceptors results in increased thermogenesis, decrease in the amount of white adipose tissue without food intake being affected, increased levels of insulin receptors, and decreased levels of serum insulin and blood glucose. The present invention may possess anti-obesity and anti-diabetic effects, which by themselves contribute to the mechanism of thermogenesis and the increase in lean body mass.

The anti-obesity and anti-diabetic effects of the present invention can be potentiated by using the compositions of the invention in combination with vanadium, in the form of vanadium organic and inorganic salts, both synthetic and naturally occurring.

The thermogenic effect of the invention may also be mediated by an increase in the activity of thyroid peroxidase, an important enzyme in thyroid hormone synthesis, an increase in the plasma levels of triiodothyronine (T3) and thyroxine (T4) with simultaneous increase in tissue oxygen uptake and increase in thermogenesis.

The thyrogenic and thermogenic effects of the present invention can be potentiated by using the compositions of the invention in combination with L-selenomethionine and iodine supplementation.

The metabolic pathways for a nutrient and drug are different in that a nutrient sustains basic metabolism, and physiological functions of the organism, while a drug is utilized as an adjunct to basic metabolism, to restore homeostasis to the physiological functions. This distinction allows one to understand the different mechanism of bioavailability of the present invention. One mechanism, as described by the prior art, is applicable primarily to sustain therapeutic levels of a drug in the organism. The other, as discussed by the present inventors, is applicable to increase absorption of nutrients and increase their metabolic utilization.

The invention is intended primarily, but not exclusively, to increase the gastrointestinal absorption of nutrients and botanical compounds. This, in general, enhances the crossing-over of nutrients and botanical compounds through biological barriers such as, but not limited to, gastrointestinal epithelium, respiratory lining, genitourinary lining, blood brain barrier and skin.

Although not wishing to be limited to any mechanism of action, it is believed that the basic mechanism of the invention is two-fold: by affecting various active and passive transport mechanisms as described in detail below; and by causing the increase for the substrate demand due to enhanced metabolism at the cellular level. This latter mechanism is triggered when the compositions and method of the invention affect thermoregulation of the body, acting directly or indirectly through activation of thermoreceptors, which results in increased thermogenesis, or metabolic heat energy production and release. By affecting thermoreceptors, particularly in the skin and mucosa, the invention prevents thermal and non-thermal nociceptive stimuli being carried to spinal dorsal horn cells, and acts as a local and general anesthetic, by increasing threshold for the nociceptive stimuli.

The compositions of the present invention may also be used to affect thermoreceptors and prevent thermal and non-thermal noxious stimuli from being carried to the dorsal horn cells, which exerts local and general analgesic affects. In addition, piperine may potentiation the analgesic affects is believed to be caused by increasing the absorption of the analgesic with which it is administered, and additionally, providing a synergistic or additive mechanism of analgesic action.

The compositions of the present invention improve gastrointestinal absorption and systemic utilization of the nutrients and nutritional supplements. Preferred embodiments elevate the maximum plasma concentration by 20–80% above the plasma concentration resulting when a regular supplement is taken alone.

The preparations of the present invention for improving gastrointestinal absorption and systemic utilization, may be made with any nutrient, biological compound, or nutritional supplement. Particularly preferred biological compounds include boswellin, curcumin, capsaicin, ashwagandha, ginkgo biloba, and aconitine.

The compositions of the present invention to improve gastrointestinal absorption and systemic utilization may also include water soluble vitamins and fat soluble vitamins. Preferred water soluble vitamins include vitamin B1, vitamin B2, niacinamide, B6, B12, folic acid, and vitamin C. The absorption of water soluble vitamins is believed to work by preventing denaturing agents present in food from altering the protein-3-tetramer hydrophilic channels which facilitate gastrointestinal absorption of water soluble vitamins. In addition, the ability of piperine to enhance gastrointestinal absorption of vitamin B12 is believed to occur by stimulating synthesis and secretion of an intrinsic factor, a glycoprotein secreted by gastric parietal cells, which facilitates transport of vitamin B12 across the cellular membrane. The preparations of the present invention used to improve gastrointestinal absorption may also contain fat soluble vitamins. Preferred fat soluble vitamins are vitamins A, vitamin D, vitamin E, and vitamin K. In addition, carotenes such as alpha-carotene, beta-carotene and transbeta-carotene are believed to be subject to enhanced absorption due to a cholagogous mechanism which increases duodenal bile salts to emulsify fat soluble vitamins, and facilitate intracellular absorption via the mixed micelle system.

The compositions of the invention may also include amino acids, particularly the essential amino acids lysine, isoleucine, leucine, threonine, valine, tryptophan, phenylalanine, and methionine. The amino acids are believed to be subject to enhanced gastrointestinal absorption by increasing the gamma-glutamyl cycle which facilitates transmembrane transport of amino acids.

Many antibiotics decrease the absorption of certain metallic and non-metallic minerals. To offset such losses, the compositions of the present invention may include essential minerals such as iodine, calcium, iron, zinc, copper, magnesium and potassium. Other metals such as vanadium, chromium, selenium and manganese may also be included in compositions of the present invention. It appears that the compositions of the present invention facilitate gastrointestinal absorption of these metallic compounds mainly by enhancing the active transport of these compounds across the membrane. In addition, the compositions of the present invention may prevent gastrointestinal absorption of certain dangerous heavy metals such as lead, mercury, and cadmium, and prevent systemic interference of the heavy metals with enzymatic functions. The compositions of the invention can form insoluble salts with mercury chloride, lead chloride and cadmium chloride and also protect sulfhydryl groups of enzymes from reacting with heavy metals.

The compositions of the present invention may also include antioxidants. Preferred antioxidants include vitamin A, vitamin C, vitamin E, alpha-carotene, transbeta-carotene, betacryptoxanthin, lycopene, lutein/zeaxanthin, pine bark bioflavonals complex, germanium, selenium, and zinc. The enhancement of antioxidant activity is believed to occur through enhanced systemic availability of antioxidant compounds through inhibition of lipid peroxidation and free radical formation. Preferred compositions of the present invention may include a variety of any of the above ingredients, which are particularly needed in a particular population.

Many of the nutrients, biological compounds and nutritional supplements which may be included in the compositions of the present invention are available commercially. Particularly, vitamin, mineral, amino acid and antioxidants are available commercially. The herbal compounds are generally used in powder form which is a dried ethanol extract of a particular plant. For example, Boswellic acid is from an ethanol extract of *Boswellia serrata* roots. Ginsenosides are from an ethanol extract of Ginseng roots. Withanaloids are from an ethanol extract of *Whitania somnifera* plant. *Gingko flavinoids* are from an ethanol extract of *Gingko biloba* plant. Curcuminoids are from ethanol extract of *Cucuma longa* plant. Pycnogenol is from an ethanol extract of *Pinus pinaseter* bark. Proanthocyanidins are from an ethanol extract of pine bark. Some of the herbal compounds are also available commercially from a variety of sources. The piperine in the invention may be produced by the new method of isolation of piperine shown in Example 14, below. The compound obtained in this manner has the trademark name of Bioperine®. Alternatively, piperine may be provided by the prior art methods or made synthetically.

The following examples are not intended to be limiting in any way, but demonstrate some of the preferred embodiments of the present invention.

EXAMPLES

NUTRITIONAL FORMULATIONS

Vitamin A tablets/capsules

| | | |
|---|---|---|
| Example 1) | Formulation: Vitamin A tablets/capsules/softgels | |
| | Vitamin A (Palmitate) | 10,000 IU |
| | Piperine | 4 mg |
| Example 2) | Vitamins A & D tablets/capsules/softgels | |
| | Vitamin A (Palmitate) | 10,000 IU |
| | Vitamin D (Calciferol) | 400 IU |
| | Piperine | 4 mg |
| Example 3) | Betacarotene capsules/softgels | |
| | Betacarotene | 15 mg |
| | Piperine | 4 mg |
| Example 4) | Curcumin Capsules | |
| | Curcumin (min. 95% of curcuminoids) | 500 mg |
| | Piperine | 5 mg |
| Example 5) | Boswellin Capsules | |
| | Boswellia Serrata Extract (65% Boswellic acid min.) | 320 mg |
| | Piperine | 3 mg |
| Example 6) | Herbal capsules/tablets | |
| | Formula A | |
| | Valerian root | 100 mg |
| | Chamomile (flower) | 100 mg |
| | Passion Flower | 25 mg |
| | Ginseng root powder | 50 mg |
| | Skullcap | 25 mg |
| | Nettle leaves | 25 mg |
| | Piperine | 3 mg |
| | Formula B | |
| | Buchu leaves | 100 mg |
| | Uva Ursi leaves | 25 mg |
| | Celery seed | 25 mg |
| | Juniper berries | 50 mg |
| | Parsley leaves | 50 mg |
| | Corn silk | 50 mg |
| | Piperine | 4 mg |
| | Formula C | |
| | Echinacea root | 100 mg |
| | Astragalus root | 100 mg |
| | Barley leaves | 50 mg |
| | Schizandra berries | 100 mg |
| | Shiitake Mushroom | 50 mg |
| | Piperine | 5 mg |

NUTRITIONAL FORMULATIONS

Vitamin A tablets/capsules

Formula D

| | | |
|---|---|---|
| | Ginseng extract (5% Ginsenosides) | 500 mg |
| | Piperine | 5 mg |

Formula E

| | | |
|---|---|---|
| | Ginseng extract | 250 mg |
| | Ashwagandha extract (1% withanaloids) | 250 mg |
| | Piperine | 5 mg |

Formula F

| | | |
|---|---|---|
| | Gingko Biloba extract (24% ginkoflavinoids) | 240 mg |
| | Piperine | 3 mg |

Formula G

| | | |
|---|---|---|
| | Boswellia Serrata extract | 320 mg |
| | Curcumin | 200 mg |
| | Piperine | 5 mg |

Formula H

| | | |
|---|---|---|
| | Boswellia Serrata extract | 320 mg |
| | Capsaicin | 3 mg |
| | Piperine | 4 mg |

Example 7) Anti-oxidant tablets/capsules

Formula A

| | | |
|---|---|---|
| | Vitamin C | 250 mg |
| | Vitamin E | 100 IU |
| | Vitamin A (Beta Carotene) | 10,000 IU |
| | Selenium (from L-Selenomethionine) | 50 μg |
| | Chromium (Chromium Picolinate) | 50 μg |
| | Piperine | 4 mg |

Formula B

| | | |
|---|---|---|
| | Pycnogenol | 30 mg |
| | Piperine | 3 mg |

Formula C

| | | |
|---|---|---|
| | Pine bark extract | 15 mg |
| | Curcumin | 15 mg |
| | Piperine | 3 mg |

Formula D (softgel)

| | | |
|---|---|---|
| | Coenzyme Q$_{10}$ | 15 mg |
| | Piperine | 3 mg |

Formula E - Anti-oxidant beverage drink

| | | |
|---|---|---|
| | Vitamin C | 200 mg |
| | Beta carotene | 15 mg |
| | Vitamin E | 100 IU |
| | Zinc (monomethionine) | 15 mg |
| | Selenium (L-Selenomethionine) | 50 μg |
| | Citrus bioflavanoid complex | 50 mg |
| | Quercetin | 25 mg |
| | Rutin | 25 mg |
| | Hesperidin (Citrus) | 20 mg |
| | Pycnogenol | 5 mg |
| | Piperine | 2.5 mg |

Example 8) Amino Acid Formulation

| | | |
|---|---|---|
| | L-Taurine | 200 mg |
| | L-Carnitine | 100 mg |
| | Piperine | 2.5 mg |

Example 9) Vitamin B Complex

| | | |
|---|---|---|
| | Pantothenic Acid (Vitamin B5) | 200 mg |
| | Niacinamide (Vitamin B5) | 125 mg |
| | Pyridoxine HCL (Vitamin B6) | 75 mg |
| | Thiamine (Vitamin B1) | 60 mg |
| | Riboflavin (Vitamin B2) | 25 mg |
| | Para-aminobenzoic acid (PABA) | 25 mg |
| | Folic acid | 400 μg |
| | Cobalamin (Vitamin B12) | 200 μg |
| | Biotin | 100 μg |
| | Piperine | 4 mg |

Example 10) Multi Vitamin

| | | |
|---|---|---|
| | Vitamin A | 5,000 IU |
| | Vitamin B1 | 1.5 mg |
| | Vitamin B2 | 1.7 mg |
| | Vitamin B6 | 2.0 mg |
| | Niacinamide | 20 mg |
| | Vitamin E | 30 IU |
| | Vitamin B12 | 6 mg |
| | Pantothenic Acid | 10 μg |
| | Vitamin D | 400 IU |
| | Vitamin C | 100 mg |
| | Folic Acid | 400 μg |
| | Biotin | 30 μg |
| | Calcium | 200 mg |
| | Magnesium | 400 mg |
| | Iron | 18 mg |
| | Iodine (Kelp) | 150 μg |
| | Copper | 2 mg |
| | Manganese | 2.5 mg |
| | Potassium | 40 mg |
| | Chromium | 25 mg |
| | Selenium | 25 mg |
| | Vitamin K1 | 25 mg |
| | Piperine | 5 mg |

Example 11) Hydroxycitric Acid

| | | |
|---|---|---|
| | Citrin ® (Calcium salt of hydroxycitric acid) | 500 mg |
| | Piperine | 5 mg |

The above formulations and ingredients are examples, and are not intended to limit the invention in any way.

Example 12

Bioavailability of Beta-carotene

The following is an example of the utilization of piperine in nutrient absorption. Piperine known under the trademark Bioperine® consisting of 98% piperine has been evaluated in a nutrient bioavailability experiment. The objective of the study was to compare the beta-carotene, in human volunteers receiving the formula with and without Bioperine®. Twelve healthy male volunteers, non-smokers, abstaining from alcohol, not taking nutritional supplements or prescription drugs during the period of cross-over study, received beta-carotene supplementation with and without Bioperine® for a period of 14 days.

TABLE 1

Formulations of beta-carotene alone and with Bioperine ® used in the 14 day double-blind, cross-over study The following formulations of beta-carotene were tested:

| | Formulation A | Formulation B |
|---|---|---|
| Beta-carotene | 15 mg | 15 mg |
| Methylcellulose | 480 mg | 480 mg |
| Bioperine ® | None | 5 mg |

Results of this study demonstrate that after 14 days of supplementation, volunteers from the control group, receiving formulation A, were found to have significantly smaller increase in blood levels of beta-carotene than those from the group receiving formulation B with Bioperine®. The group receiving Bioperine® had almost a two fold increase in blood beta-carotene levels as compared to the group receiving beta-carotenes only.

TABLE 2

Blood levels of beta-carotene after 14 days supplementation of beta-carotene alone or beta-carotene with Bioperine ®

Pharmacokinetic parameters for beta-carotene

|  | Formulation A | Formulation B |
| --- | --- | --- |
| Maximum plasma conc. ug/dl | 47.2 + 6.4 | 65.8 + 9.7** |
| AUC* ug/dl/day | 272.0 + 47.6 | 435.2 + 74.2** |

*Area under the plasma beta-carotene during 14 day supplementation
**highly significant (p < 0.001).

The probable mechanism of piperine's effect on the bioavailability of beta-carotene is its effect on gastrointestinal events that lead to increased absorption of this nutrient and most probably other nutrients as well.

A dose of 5 mg of piperine, and up to 15 mg, would most likely not interfere with the metabolism of a majority of drugs as previously discussed. In fact, this dose as used with beta-carotene does not affect the metabolic pathways of this nutrient in the body, as measured by the blood levels of retinol which remained unchanged throughout the experiment (see below). Retinol, or vitamin A, is a product of metabolic conversion of beta-carotene, and its blood levels would likely be affected by enzymatic inhibition/stimulation with piperine. It is an important finding that piperine does not elevate the conversion of beta-carotene to vitamin A, since toxic effects due to an overdose of vitamin A are well known. The benefit of increased blood levels of beta-carotene without danger of vitamin A toxicity translates into the safe and effective enhancement of anti-oxidant protection provided by beta-carotene.

TABLE 3

Values of Vitamin A (retinol) before treatment and after 14 days supplementation with Bioperine ®

| Formulations | Before treatment (ug/dL) | Day 14 (ug/dL) |
| --- | --- | --- |
| A | 66.0 + 11.5 | 65.1 + 10.2* |
| B | 65.2 + 11.9 | 65.0 + 10.6* |

*difference not statistically significant

Additional evidence from the experiment with 14 day supplementation of beta-carotene to 12 healthy volunteers show that piperine does not affect absorption, metabolism and elimination of nutrients that are not supplemented, but otherwise consumed with a daily food. For example, the blood levels of water soluble vitamin C and lipid soluble vitamin E, which were not supplemented, were not affected as assessed before the study and after completion of 14 day supplementation of beta-carotene with piperine.

TABLE 4

Comparison of vitamin C blood levels before and after 14 day supplementation with beta-carotene or beta-carotene with Bioperine ®

| Formulations | Before treatment (ug/dl) | Day 14 (ug/dl) |
| --- | --- | --- |
| A | 0.62 + 0.13 | 0.64 + 0.10* |
| B | 0.66 + 0.12 | 0.65 + 0.11* |

*difference not statistically significant

TABLE 5

Comparison of vitamin E blood levels before and after 14 day supplementation with beta-carotene or beta-carotene with Bioperine ®

| Formulations | Before treatment (ug/dl) | Day 14 (ug/dl) |
| --- | --- | --- |
| A | 0.80 + 0.18 | 0.84 + 0.15* |
| B | 0.83 + 0.16 | 0.84 + 0.16* |

*difference not statistically significant

The apparent lack of any inhibitory effect from piperine on human metabolism at low doses is an important observation. This is particularly so because many of those who may require piperine co-administered with a nutrient like certain vitamins, may also be on a drug regimen which can not be altered. Based on the available literature, a dose of piperine below 20 mg per day per person should not affect the metabolism of most if not all xenobiotics such as the drugs discussed above.

Example 13

Toxicity

Black pepper, which contains approximately 5–9% of piperine, is listed by the FDA as an herb generally recognized as safe (GRAS) for its intended use as a spice, seasoning and flavoring (21 CFR 100.0, 182.10, 182.20). Based on black pepper imports, it is estimated that the average consumption of black pepper in the United States is about 359 mg/person/day*. This amount of crude pepper translates to 18.0–32.3 mg of piperine/person/day [Table 6].

TABLE 6

Estimated average human consumption of black pepper/piperine*

|  | mg/person | mg/kg** |
| --- | --- | --- |
| Black pepper daily | 359 | 6.0 |
| Piperine daily | 18.0–32.3 | 0.3–0.54 |

*Data based on doctoral thesis by Shore Scott Kindell, Drexel University, 1984.
**Average weight of a person estimated at 60 kg.

According to other sources daily human consumption of black pepper constitutes 0.02% of the diet, which corresponds to 2 mg of powdered pepper/kg/day (Bhat, G. B. Chandrasekhara, N. (1986), "Lack of adverse effect of piperine, pepper or pepper oleoresin on weanling rats", *J. Food Safety*, 7; pp. 215–223). Based on this assumption, black pepper, and its components oleoresin containing 40% piperine, and pure piperine, were fed to rats at doses calculated as 5 to 20 times the average daily intake for humans. This particular diet with pepper and its components did not affect food intake, growth pattern of fed animals, the organ weights, and produced no clinical symptoms. Comparison of the blood chemistry tests results of the treated and untreated animals showed no alterations in RBC, WBC, the differential count, levels of hemoglobin, total serum proteins, albumins, globulins, glucose, cholesterol and levels of serum aminotransferases and phosphatases.

Acute, subacute and chronic toxicity studies of piperine in laboratory animals indicate that piperine used in broad range of doses, does not cause any abnormality in the general growth pattern, body to organ weight ratio, clinical symptomatology and blood chemistry data (Johri, R. K., Zutshi, U. (1992), "An Ayurvedic formulation 'Trikatu' and its constituents", *Journal of Ethnopharmacology*, 37; pp. 85–91). The dose of piperine considered as bioenhancing absorption of nutrients is considered 0.0004–0.15 mg of piperine/kg body weight. That is many thousand times less than the $LD_{50}$ dose (dose toxic to 50% animal tested) of piperine established in mice and rats [Table 7]. The $LD_{50}$ data indicate a relatively high therapeutic index for piperine, which means high degree of safety in nutritional use of piperine.

TABLE 7

Piperine $LD_{50}$ dose established in rodents (Johri, R.K., Zutshi, U. (1992), "An Ayurvedic formulation 'Trikatu' and its constituents", Journal of Ethnopharmacology, 37; pp. 85–91 and Plyachaturawat, P. et al. (1983), "Acute and sub-acute toxicity of piperine in mice, rats and hamsters", Toxicology Letters, 16; pp. 351–359).

| Experimental animal | $LD_{50}$ mg/kg body weight |
|---|---|
| Mice | 1,638.6 |
| Mice | 330.0 |
| Rat weanling | 585.0 |
| Rat | 514.0 |
| Rat | 800.0 |

Piper species have been traditionally used to induce abortion. The reported antifertility property of piperine was investigated in laboratory animals (Plyachaturawat, P. et al. (1982), "Post-coital antifertility effect of piperine", *Contraception*, 26; pp. 625–633 and Kholkute, S. E. et al. (1979), "Antifertility activity of the fruits of *piper longum* in female rats", *Indian J. Exp. Biol.*, 17; 289–290). Piperine inhibited significantly pregnancy in mice when given by either intraperitoneal or oral route of administration at a dose of 12.5 mg/kg body weight, twice a day. Piperine was effective at both pre- and post-implantation periods. However, when used in a dose of 5 mg/kg body weight/day, which is approximately 70 times more than the bioenhancing dose, piperine had no anti-fertility activity in mice. The dose of piperine that significantly inhibited pregnancy in mice did not interfere with the estrogen cycle, did not show uterotropic effect, and did not produce clinically noticeable toxicity. The mechanism of anti-fertility action of piperine is not known at present, but it does not operate through a hormonal mechanism or uterotonic activity.

Black pepper extracts have been shown to possess tumor inhibitory activity (Loder, J. W. et al. (1969), "Tumor inhibitory plants", *Aust J. Chem.*, 22; pp.1531–1538), but one report points to a possibility of carcinogenic effect of black pepper (Concon, J. M. et al (1979), "Black pepper: Evidence of carcinogencitiy", *Nutrition and Cancer*, 1; pp. 22–26). In this study an ethanol extract of black pepper at a dose calculated as 400 to 700 times higher than the pharmacologically effective dose of piperine, has been applied topically to mice for three months. This treatment resulted in the significant increase in tumor occurrence in mice. The authors of this report discuss several chemicals that are known components in black pepper extracts as possible culprits. Safarole, tanins and terpenoids like d-limonene, 1-pinene, linalool and phellandrene are specifically mentioned as potential carcinogens, cocarcinogens, or tumor promoters. Piperine has not been implicated directly by the report as a possible tumorigenic compound, but because it contains the methylendioxybenzene structure in common with safarole, chavicine, piperittine and myristicine may be problematic. However, experiments dealing with piperine and safarole metabolism have shown that despite chemical likeness, piperine and safarole are metabolized differently, giving rise to different types of products (Ionnoids, C. et al. (1981), "Safrole: Its metabolism, carcinogenicity and interactions with cytochrome P-450", *Food and Cosmetics Toxicology*, 19; pp. 657–666 and Bhat, B. G., Chandrasekhara, N. (1987), "Metabolic Disposition of Piperine in the Rat", *Toxicology*, 44: pp. 99–106). Piperine and safarole interact differently with rat liver microsomes, and those differences may be attributed to the structural dissimilarities in the side chain of these two compounds (Wrba, H. et al. (1992) "Carcinogenicity testing of some constituents of black pepper (*Piper nigrum*), 44(2); pp. 61–65.) For example, the cytochrome P-450 content of hepatic microsomes decreased by approximately 20% due to treatment of rats with piperine, whereas safarole pretreatment increased the cytochrome P-450 content by about 50%.

In a separate experiment, preweaned mice injected with safarole, tannic acid or methylcholantrene, a reference carcinogen, developed tumors. Safarole and tannic acid have been shown to be weak carcinogens when compared with methylcholantrene. Feeding of d-limonene to the mice which were injected with any of the above three substances reduced their carcinogenic activity. Feeding piperine to the mice receiving the three compounds did not modify their carcinogenic activity (Wrba, H. et al. (1992) "Carcinogenicity testing of some constituents of black pepper (*Piper nigrum*), 44(2); pp. 61–65).

Owing to its interaction with xenobiotic-metabolizing enzymes, piperine may potentially inhibit detoxification of some toxic compounds. To investigate this possibility the in vitro influence of piperine on various enzymes that are closely related to the metabolism and detoxification system of a toxic compound such as benzo(a)pyrene has been studied (Chu, C. Y. et al. (1994), "Modulatory effect of piperine on benzopyrene-induced cytotoxicity and DNA adduct formation in V-79 lung fibroblasts", *Food and Chem. Toxicol.*, 32 (4); pp. 373–377). This study showed that piperine significantly enhanced benzo(a)pyrene cytotoxicity in vitro. The results of this study are contradicted, however, by another report indicating that piperine can in fact inhibit benzo(a)pyrene activation, by lowering benzo(a)pyrene-oxide production, thus decreasing benzo(a)pyrene cytotoxicity (Atal, C. K. et al. (1985), "Biochemical basis of enhanced drug bioavialability by piperine: evidence that piperine is a potent inhibitor of drug metabolism", *J. Pharmacol. Exp. Therap.*, 232; pp. 258–262).

Alteration of hepatic mixed function oxidases may potentially lead to hepatotoxic effect. Piperine was evaluated for potential hepatotoxicity in rats (Dalvi, R. R., Dalvi, P. S. (1991) "Differences in the effect of piperine and piperonyl butoxide on hepatic drug metabolizing enzymes in rats", *Drug Metabl. Drug Interact*, 9 (1); pp. 23–30). Piperine was administered to the animals intragastrically in doses 100 mg and 800 mg/kg, and intra-peritoneally in doses 10 mg/kg and 100 mg/kg. None of the treatment regiments altered significantly the following liver enzymes indicative of liver damage: serum sorbitol dehydrogenase (SDH), alanine aminotransferase (ALT), aspartate aminotransferase (AST) and isocitrate dehydrogenase (ICD).

In a separate study piperine was found to have a hepatoprotective action in mice treated with potent hepatotoxins tetra-hydroperoxide and carbon tetrachloride (Koul, I. B., Kapil, A. (1993), "Evaluation of the liver protective potential of piperine, an active principle of black and long peppers", *Planta Med.,* 59(5); pp. 413–417). This protective effect, demonstrated by both in vivo and in vitro experiments, was explained by piperine mediated decrease in lipid peroxidation, and reduction in hepatocellular damage as measured by reduced enzymatic leakage of glutamate pyruvate transaminase and alkaline phosphatase. Piperine also prevented depletion of reduced glutathione and total thiols in the liver. The reduced glutathione is one of the most important biomolecules in protection against chemically induced cytotoxicity, and can eliminate toxic compounds by conjugation.

The effect of piperine on lipid peroxidation and liver enzymes was confirmed in other studies, which show piperine inhibiting lipid peroxide formation and leveling off increased levels of acid phosphatase in rats injected with carageenin—a compound which is known to stimulate liver peroxide formation (Dhuley, J. N. et al. (1993), "Inhibition of lipid peroxidation by piperine during experimental inflammation in rats", *Ind. J. Exp. Biol.,* 31; pp. 443–445). Liver peroxide output is increased as a result of damage of lysosomes probably elicited indirectly by inflammatory action of carageenin, with subsequent increased levels of liver lipid peroxidation and acid phosphatase.

The nitrosation reaction of piperine is of concern, as endogenous nitrosation could take place in the human stomach from ingested piperine and nitrites (Wakabayashi, K. et al. (1989), "Mutagens and carcinogens produced by the reaction of environmental aromatic compounds with nitrite", *Canc. Surv.,* 8(2); pp. 385–399). This combination may lead to potentially mutagenic products. Nitrites can be ingested by consuming cured foods, such as meat and, in particular, bacon. Nonetheless, research data indicate a remote possibility of any potential nitrosation reaction of piperine, for the following reasons:

average consumption of pepper for culinary purposes and proposed dose of piperine for pharmacological effects are well below doses of piperine required for the significant nitrosation reaction to occur;

a number of food constituents, such as ascorbic acid, tocopherols, plant phenolics and flavanoids exert protective effect against nitro derivatives formation. Thus, nitro compounds formation with piperine, if any, would be a multifactorial and competitive event;

recent study indicates that due to awareness of deleterious health effects of the volatile nitrosamines, a continuously lowering trend in the levels of volatile nitrosamines in all types of food, with exception of fried bacon, is being noticed.

The doses of piperine, recommended for bioavailability enhancement are relatively low when compared to the toxic doses, and translate to a dose of pure piperine in a range of 2.5 to 5 mg per dose. That dose equals to an average daily dose of 0.04–0.25* mg of piperine/kg body weight [Table 8].

TABLE 8

Average human consumption of piperine as a bioenhancing compound

|  | mg/person | mg/kg** |
|---|---|---|
| Bioperine ® daily | 2.5–15* | 0.04–0.25 |
| Bioperine ® monthly | 75–450 | 1.25–7.5 |
| Bioperine ® yearly | 900–5,400 | 15–900 |

*Daily dose calculated based on lowest and highest estimated dose of Bioperine ® used as bioenhancing supplement 1–3 times daily.
**Average weight of a person estimated at 60 kg.

Example 14

A preparation obtained in a unique manufacturing process.

Commercially available Black pepper oleoresin or Long pepper oleoresin is used as the source of piperine. Ground up Black pepper or Long pepper can also be used.

To a mixture of butanol and hexane (35 liters), 35 kg Black pepper oleoresin is added and heated to 40° C. The mixture is then cooled and filtered.

The precipitate is washed with Butanol/hexane mixture to obtain crude piperine.

The crude piperine is dissolved in methanol at 60° C. and treated with alumina and charcoal by stirring. It is then filtered and concentrated under vacuum to obtain a powder.

Bioperine®

Material thus prepared has the following specifications:
  Color: Pale yellow crystalline powder
  Melting range: 128 degrees–131 degrees Celsius
  Assay: min. 98% pure piperine (by HPLC)

We claim:

1. A method of increasing nutrient bioavailability in a subject desiring such an increase, comprising administering to said patient a nutritionally effective amount of at least one nutritional material and a bioavailability enhancing amount of piperine.

2. A method as recited in claim 1, wherein said piperine comprises at least one member selected from the group consisting of synthetically made piperine, extract from black pepper and extract from *piper longum.*

3. A method as recited in claim 1, wherein said administering comprises topically applying or parenterally administering to said subject a composition comprising piperine in an amount of from about 0.00004 to about 0.015 mg/kg of body weight of said subject.

4. A method as recited in claim 1, wherein said administering comprises orally administering to said subject a composition comprising piperine in an amount of from about 0.0004 to about 0.15 mg/kg of body weight of said patient.

5. A method as recited in claim 1, wherein said subject is a human or an animal.

6. A method as recited in claim 1, wherein said piperine is administered in an amount in the range of from about 0.00004 mg to about 0.15 mg per kg of weight of said subject per day.

7. A method as recited in claim 1, wherein said nutritional material comprises at least one material selected from the group consisting of herbal extracts, water-soluble vitamins, fat-soluble vitamins, amino acids, minerals and antioxidants.

8. A method as recited in claim 7, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

9. A method of increasing nutrient bioavailability in a subject desiring such an increase, comprising administering to said subject a nutritionally effective amount of at least one nutritional material and a potentiating amount of an extract of black pepper, said extract of black pepper having a higher concentration of piperine than natural black pepper.

10. A method as recited in claim 9, wherein said administering comprises topically applying or parenterally administering to said subject a composition comprising piperine in an amount of from about 0.00004 to about 0.015 mg/kg of body weight of said subject.

11. A method as recited in claim 9, wherein said administering comprises orally administering to said subject a composition comprising piperine in an amount of from about 0.0004 to about 0.15 mg/kg of body weight of said subject.

12. A method as recited in claim 9, wherein said subject is a human or an animal.

13. A method as recited in claim 9, wherein said piperine is administered in an amount in the range of from about 0.00004 mg to about 0.15 mg per kg of weight of said subject per day.

14. A method as recited in claim 9, wherein said nutritional material comprises at least one material selected from the group consisting of herbal extracts, water-soluble vitamins, fat-soluble vitamins, amino acids, minerals and antioxidants.

15. A method as recited in claim 14, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

16. A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine.

17. A method as recited in claim 16, wherein said piperine comprises at least one member selected from the group consisting of synthetically made piperine, extract from black pepper and extract from *piper longum.*

18. A method as recited in claim 16, wherein said administering comprises topically applying or parenterally administering to said subject a composition comprising piperine in an amount of from about 0.00004 to about 0.015 mg/kg of body weight of said subject.

19. A method as recited in claim 16, wherein said administering comprises orally administering to said subject a composition comprising piperine in an amount of from about 0.0004 to about 0.15 mg/kg of body weight of said subject.

20. A method as recited in claim 16, wherein said subject is a human or an animal.

21. A method as recited in claim 16, wherein said piperine is administered in an amount in the range of from about 0.00004 mg to about 0.15 mg per kg of weight of said subject per day.

22. A method as recited in claim 16, wherein said nutritional material comprises at least one material selected from the group consisting of herbal extracts, water-soluble fat-soluble vitamins, amino acids, minerals and antioxidants.

23. A method as recited in claim 22, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine, L-selenomethionine, and said minerals are selected from the group consisting of calcium, iron, zinc, vanadium, selenium, chromium, iodine, potassium, manganese, copper and magnesium.

24. A method of improving gastrointestinal absorption and systemic utilization of nutritional materials in a subject desiring such improvement, comprising administering to said subject a nutritionally effective amount of at least one nutritional material and a potentiating amount of an extract of black pepper, said extract of black pepper having a higher concentration of piperine than natural black pepper.

25. A method as recited in claim 24, wherein said administering comprises topically applying or parenterally administering to said subject a composition comprising piperine in an amount of from about 0.00004 to about 0.015 mg/kg of body weight of said subject.

26. A method as recited in claim 24, wherein said administering comprises orally administering to said subject a composition piperine in an amount of from about 0.0004 to about 0.15 mg/kg of body weight of said subject.

27. A method as recited in claim 24, wherein said subject is a human or an animal.

28. A method as recited in claim 24, wherein said piperine is administered in an amount in the range of from about 0.00004 mg to about 0.15 mg per kg of weight of said subject per day.

29. A method as recited in claim 24, wherein said nutritional material comprises at least one material selected from the group consisting of herbal extracts, water-soluble vitamins, fat-soluble vitamins, amino acids, minerals and antioxidants.

30. A method as recited in claim 29, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

31. A method of providing an increase in nutrient induced thermogenesis in a subject desiring such an increase, comprising administering to said subject a nutritionally effective amount of at least one nutritional material and a nutrient induced thermogenesis enhancing amount of piperine.

32. A method as recited in claim 31, wherein said piperine comprises at least one member selected from the group consisting of synthetically made piperine, extract from black pepper and extract from *piper longum.*

33. A method as recited in claim 31, wherein said administering comprises topically applying or parenterally administering to said subject a composition comprising piperine in an amount of from about 0.00004 to about 0.015 mg/kg of body weight of said subject.

34. A method as recited in claim 31, wherein said administering comprises orally administering to said subject a composition comprising piperine in an amount of from about 0.0004 to about 0.15 mg/kg of body weight of said subject.

35. A method as recited in claim 31, wherein said subject is a human or an animal.

36. A method as recited in claim 31, wherein said piperine is administered in an amount in the range of from about 0.00004 mg to about 0.15 mg per kg of weight of said subject per day.

37. A method as recited in claim 31, wherein said nutritional material comprises at least one material selected from the group consisting of herbal extracts, water-soluble vitamins, fat-soluble vitamins, amino acids, minerals and antioxidants.

38. A method as recited in claim 37, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

39. A method of providing an increase in nutrient induced thermogenesis in a subject desiring such an increase, comprising administering to said subject a nutritionally effective amount of at least one nutritional material and a potentiating amount of an extract of black pepper, said extract of black pepper having a higher concentration of piperine than natural black pepper.

40. A method as recited in claim 39, wherein said administering comprises topically applying or parenterally administering to said subject a composition comprising piperine in an amount of from about 0.00004 to about 0.015 mg/kg of body weight of said subject.

41. A method as recited in claim 39, wherein said administering comprises orally administering to said subject a composition comprising piperine in an amount of from about 0.0004 to about 0.15 mg/kg of body weight of said subject.

42. A method as recited in claim 39, wherein said subject is a human or an animal.

43. A method as recited in claim 39, wherein said piperine is administered in an amount in the range of from about 0.00004 mg to about 0.15 mg per kg of weight of said subject per day.

44. A method as recited in claim 39, wherein said nutritional material comprises at least one material selected from the group consisting of herbal extracts, water-soluble -vitamins, fat-soluble vitamins, amino acids, minerals and antioxidants.

45. A method as recited in claim 44, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

46. A method of providing an increase in lean body mass in a subject desiring such an increase, comprising administering to said subject a nutritionally effective amount of at least one nutritional material and a lean body mass enhancing amount of piperine.

47. A method as recited in claim 46, wherein said piperine comprises at least one member selected from the group consisting of synthetically made piperine, extract from black pepper and extract from *piper longum.*

48. A method as recited in claim 46, wherein said administering comprises topically applying or parenterally administering to said subject a composition comprising piperine in an amount of from about 0.00004 to about 0.015 mg/kg of body weight of said subject.

49. A method as recited in claim 46, wherein said administering comprises orally administering to said subject a composition comprising piperine in an amount of from about 0.0004 to about 0.15 mg/kg of body weight of said subject.

50. A method as recited in claim 46, wherein said subject is a human or an animal.

51. A method as recited in claim 46, wherein said piperine is administered in an amount in the range of from about 0.0004 mg to about 0.15 mg per kg of weight of said subject per day.

52. A method as recited in claim 46, wherein said nutritional material comprises at least one material selected from the group consisting of herbal extracts, water-soluble vitamins, fat-soluble vitamins, amino acids, minerals and antioxidants.

53. A method as recited in claim 52, wherein said herbal extracts are selected from the group consisting of curcumin, boswellin, ashwagandha, *ginkgo biloba,* capsaicin and aconitine, said water-soluble vitamins are selected from the group consisting of vitamin 131, vitamin B2, niacinamide, vitamin B6, vitamin B12, folic acid and vitamin C, said fat-soluble vitamins are selected from the group consisting of vitamin A, vitamin D, vitamin E and K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

54. A method of providing an increase in lean body mass in a subject desiring such an increase, comprising administering to said subject a nutritionally effective amount of at least one nutritional material and a potentiating amount of an extract of black pepper, said extract of black pepper having a higher concentration of piperine than natural black pepper.

55. A method as recited in claim 54, wherein said administering comprises topically applying or parenterally administering to said subject a composition comprising piperine in an amount of from about 0.00004 to about 0.015 mg/kg of body weight of said subject.

56. A method as recited in claim 54, wherein said administering comprises orally administering to said subject a composition comprising piperine in an amount of from about 0.0004 to about 0.15 mg/kg of body weight of said subject.

57. A method as recited in claim 54, wherein said subject is a human or an animal.

58. A method as recited in claim 54, wherein said piperine is administered in an amount in the range of from about 0.00004 mg to about 0.15 mg per kg of weight of said subject per day.

59. A method as recited in claim 54, wherein said nutritional material comprises at least one material selected from the group consisting of herbal extracts, water-soluble vitamins, fat-soluble vitamins, amino acids, minerals and antioxidants.

60. A method as recited in claim 59, wherein said herbal extracts are selected from the group consisting of curcumin, boswellin, ashwagandha, *ginkgo biloba,* capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbeta-carotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

* * * * *

UNITED STATES PATENT AND TRADEMARK OFFICE
CERTIFICATE OF CORRECTION

PATENT NO. : 5,972,382 C1
DATED : March 4, 2003
INVENTOR(S) : Muhammed Majeed et al.

It is certified that error appears in the above-identified patent and that said Letters Patent is hereby corrected as shown below:

Title page,
Item [73], Assignee, replace "Sami Chemical & Extraces (P) Ltd." with -- Sabinsa Corporation and Sami Chemical & Extracts (P) Ltd. --;

Columns 1-6,
In the second to the last lines of claims 4, 11, 19, 26, 35, 41 and 49, replace "from 0.0004" with -- from about 0.0004 --;

Column 4,
Lines 24 and 34, replace "mount" with -- amount --; and

Column 7,
Line 23, replace "from 0.0004" with --from about 0.0004 --;

Column 8,
Line 60, replace "0.0004" with -- 0.00004 --.

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 5,972,382 C1
DATED : March 4, 2003
INVENTOR(S) : Muhammed Majeed et al.

It is certified that error appears in the above-identified patent and that said Letters Patent is hereby corrected as shown below:

Column 1,
Line 30, replace "adminstering" with -- administering --;
Line 34, replace "from 0.0004" with -- from about 0.0004 --;
Line 35, replace "patient" with -- subject --;
Lines 38, 48, 58 and 67, replace "patient" with -- subject --;
Line 53, replace "or" with -- of --;
Line 56, replace "bioavilability on" with -- bioavailability of --;
Line 60, replace "enhancnig" with -- enhancing --;

Column 2,
Line 39, replace "from 0.0004" with -- from about 0.0004 --;
Line 39, replace "patient" with -- subject --;

Column 3,
Line 3, delete the second period;
Line 28, replace "from 0.0004" with -- from about 0.0004 --;

Column 4,
Line 6, replace "mount" with -- amount --;
Line 14, replace "mount" with -- amount --;
Line 19, replace "from 0.0004" with -- from about 0.0004 --;
Line 19, replace "patient" with -- subject --;
Line 26, replace "mount" with -- amount --;
Line 37, replace "mount" with -- amount --;
Line 41, replace "consisitng" with -- consisting --;

Column 5,
Line 4, replace "from 0.0004" with -- from about 0.0004 --;
Line 6, replace "thermogenosis" with -- thermogenesis --;
Line 58, replace "from 0.0004" with -- from about 0.0004 --;
Line 58, replace "patient" with -- subject --;

Column 6,
Line 41, replace "from 0.0004" with -- from about 0.0004 --;
Line 41, replace "patient" with -- subject --;

Column 7,
Line 25, replace "patient" with -- subject --;
Line 25, replace "0.0004" with -- about 0.0004 --;

UNITED STATES PATENT AND TRADEMARK OFFICE
CERTIFICATE OF CORRECTION

PATENT NO. : 5,972,382 C1
DATED : March 4, 2003
INVENTOR(S) : Muhammed Majeed et al.

It is certified that error appears in the above-identified patent and that said Letters Patent is hereby corrected as shown below:

Column 8,
Line 11, replace "mount" with -- amount --;
Line 67, replace "0.0004" with -- about 0.0004 --;

Column 9,
Line 1, replace "protentiating" with -- potentiating --; and

Column 11,
Line 12, replace "vanadiuum" with -- vanadium --.

Signed and Sealed this

Fourteenth Day of December, 2004

JON W. DUDAS
*Director of the United States Patent and Trademark Office*

(12) REEXAMINATION CERTIFICATE (4746th)
United States Patent
Majeed et al.

(10) Number: US 5,972,382 C1
(45) Certificate Issued: Mar. 4, 2003

(54) USE OF PIPERINE AS A BIOAVAILABILITY ENHANCER

(75) Inventors: Muhammed Majeed, Piscataway, NJ (US); Vladimir Badmaev, Piscataway, NJ (US); R. Rajendran, Bangalore (IN)

(73) Assignee: Sami Chemical & Extraces (P) Ltd., Bangalore (IN)

Reexamination Request:
No. 90/006,250, Mar. 19, 2002

Reexamination Certificate for:
Patent No.: 5,972,382
Issued: Oct. 26, 1999
Appl. No.: 09/005,594
Filed: Jan. 12, 1998

(*) Notice: This patent is subject to a terminal disclaimer. 09/005,594

Related U.S. Application Data

(60) Division of application No. 08/550,496, filed on Oct. 30, 1995, now Pat. No. 5,744,161, which is a continuation-in-part of application No. 08/393,738, filed on Feb. 24, 1995, now Pat. No. 5,536,506.

(51) Int. Cl.$^7$ .............. A61K 9/20; A61K 9/70; A61K 9/48; A61F 2/02; A61F 6/06
(52) U.S. Cl. .............. 424/464; 424/423; 424/430; 424/434; 424/443; 424/451; 424/734; 424/752; 424/756

(56) References Cited

U.S. PATENT DOCUMENTS 5,972,382 A 10/1999 Majeed et al. .............. 424/464

OTHER PUBLICATIONS

Annamalai et al., Effects of 'Trikatu' and its Individual Components and Piperine on Gastro Intestinal Tracts: Trikatu—A Bioavailable Enhancer, Indian Drugs 27, Sep. 28, 1989, pp. 595–604.

Primary Examiner—James M. Spear

(57) ABSTRACT

Compositions and methods for the improvement of gastrointestinal absorption and systemic utilization of nutrients and nutritional supplements, wherein the compositions comprise a minimum of 98% of pure alkaloid piperine. The method comprises oral, topical, or parenteral administration of the compositions of the invention. A new process for the extraction and purification of piperine is also disclosed.

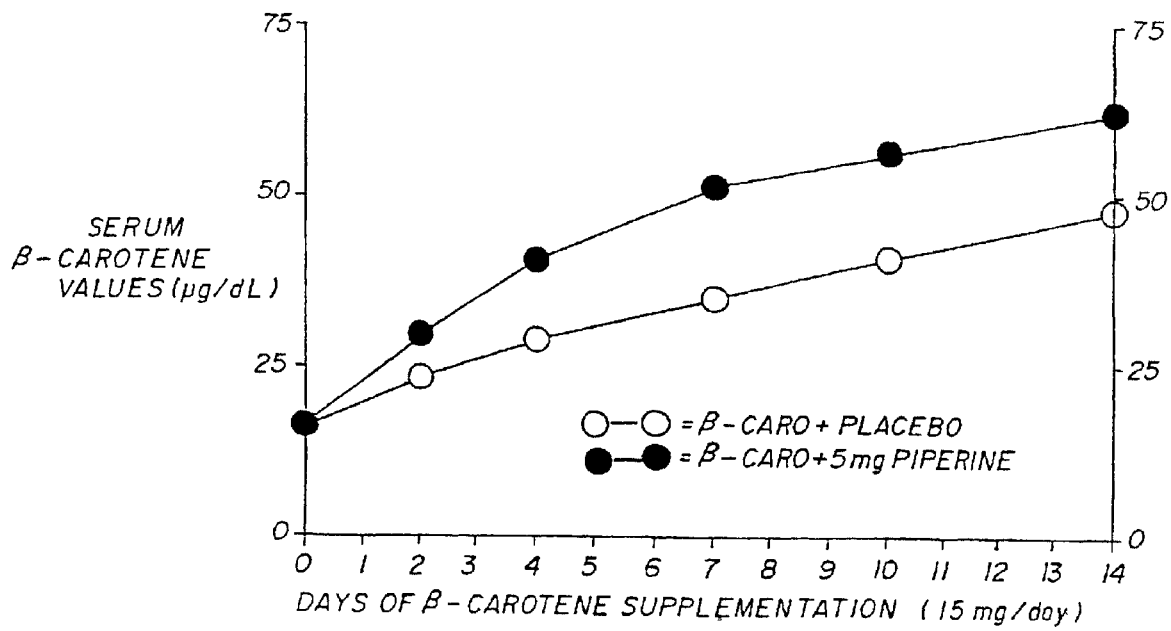

US 5,972,382 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5, 12, 20, 27, 35, 42, 50 and 57 are cancelled.

Claims 1, 3, 4, 6, 7, 9–11, 13, 14, 16, 18, 19, 21, 22, 24–26, 28, 29, 31, 33, 34, 36, 37, 39, 40, 41, 43, 44, 46, 48, 49, 51, 52, 54–56, 58 and 59 are determined to be patentable as amended.

Claims 2, 8, 15, 17, 23, 30, 32, 38, 45, 47, 53 and 60, dependent on an amended claim, are determined to be patentable.

New claims 61–120 are added and determined to be patentable.

1. A method of increasing nutrient bioavailability in a subject desiring such an increase, comprising adminstering to said [patient] *subject* a nutritionally effective amount of at least one nutritional material and a bioavailability enhancing amount of piperine *in an amount of no more than 15 mg per day, wherein said subject is an adult human.*

3. [A method as recited in claim 1.] *A method of increasing nutrient bioavailability in a subject desiring such an increase, comprising administering to said patient a nutritionally effective amount of at least one nutritional material and a bioavailability enhancing amount of piperine wherein* said administering comprises topically applying or parenterally administering to said subject a composition comprising piperine in an amount of from about 0.00004 to about 0.015 mg/kg of body weight of said subject.

4. [A method as recited in claim 1.] *A method of increasing nutrient bioavailability in a subject desiring such an increase, comprising administering to said patient a nutritionally effective amount of at least one nutritional material and a bioavailability enhancing amount of piperine wherein* said administering comprises orally administering to said subject a composition comprising piperine in an amount of from 0.0004 to about 0.15 mg/kg of body weight or said patient.

6. [A method as recited on claim 1.] *A method of increasing nutrient biovavilability on a subject desiring such an increase, comprising administering to said patient a nutritionally effective amount of at least one nutritional material and a bioavailability enhancnig amount of piperine wherein* said piperine is administered in an amount in the range of from about 0.00004 to about 0.15 mg per kg of weight of said subject per day.

7. A method [as recited in claim 1] *of increasing nutrient bioavailability in a subject desiring such an increase, comprising administering to said patient a nutritionally effective amount of at least one nutritional material and a bioavailability enhancing amount of piperine*, wherein said nutritional material comprises at least one material selected from the group consisting of herbal extracts, water-soluble vitamins, fat-soluble vitamins, amino acids, minerals and antioxidants.

9. A method of increasing nutrient bioavailability in a subject desiring such an increase, comprising administering to said subject a nutritionally effective amount of at least one nutritional material and a potentiating amount of an extract of black pepper *that provides piperine in an amount of no more than 15 mg per day, said extract of black pepper having a higher concentration of piperine than natural black pepper, wherein said subject is an adult human.*

10. [A method as recited in claim 9.] *A method of increasing nutrient bioavailability in a subject desiring such an increase, comprising administering to said subject a nutritionally effective amount of at least one nutritional material and a potentiating amount of an extract of black pepper, said extract of black pepper having a higher concentration of piperine than natural black pepper* wherein said administering comprises topically applying or parenterally administering to said subject a composition comprising piperine in an amount of from about 0.00004 to about 0.015 mg/kg of body weight of said subject.

11. [A method as recited in claim 9.] *A method of increasing nutrient bioavailability in a subject desiring such an increase, comprising administering to said subject a nutritionally effective amount of at least one nutritional material and a potentiating amount of an extract of black pepper, said extract of black pepper having a higher concentration of piperine than natural black pepper* wherein said administering comprises orally administering to said subject a composition comprising piperine in an amount of from 0.0004 to about 0.15 mg/kg of body weight of said patient.

13. [A method as recited in claim 9.] *A method of increasing nutrient bioavailability in a subject desiring such an increase, comprising administering to said subject a nutritionally effective amount of at least one nutritional material and a potentiating amount of an extract of black pepper, said extract of black pepper having a higher concentration of piperine than natural black pepper* wherein said piperine is administered in an amount in the range of from about 0.00004 to about 0.15 mg/per kg of weight of said subject per day.

14. A method [as recited in claim 9] *of increasing nutrient bioavailability in a subject desiring such an increase, comprising administering to said subject a nutritionally effective amount of at least one nutritional material and a potentiating amount of an extract of black pepper, said extract of black pepper having a higher concentration of piperine than natural black pepper*, wherein said nutritional material comprises at least one material selected from the group consisting of herbal extracts, water-soluble vitamins, fat-soluble vitamins, amino acids, minerals and antioxidants.

16. A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine *in an amount of no more than 15 mg per day, wherein said subject is an adult human..*

18. [A method of recited in claim 16,] *A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine* wherein said administering comprises topically applying or parenterally administering to said subject a composition comprising piperine in an amount of from about 0.00004 to about 0.015 mg/kg of body weight of said subject.

19. [A method as recited in claim 16,] *A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine* wherein said administering comprises orally administering to said subject a composition comprising piperine in an amount of from 0.0004 to about 0.15 mg/kg of body weight of said subject.

21. [A method as recited in claim 16,] *A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine* wherein said piperine is administered in an amount in the range of from about 0.00004 mg to about 0.15 mg per kg of weight of said subject per day.

22. A method [as recited in claim 16] *of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine,* wherein said nutritional material comprises at least one material selected from the group consisting of herbal extracts, water-soluble *vitamins*, fat-soluble vitamins, amino acids, minerals and antioxidants.

24. A method of improving gastrointestinal absorption and systemic utilization of nutritional materials in a subject desiring such improvement, comprising administering to said subject a nutritionally effective amount of at least one nutritional material and a potentiating amount of an extract of black pepper *that provides piperine in an amount of no more than 15 mg per day,* said extract of black pepper having a higher concentration of piperine than natural black pepper, *wherein said subject is an adult human.*

25. A method [recited in claim 24,] *of improving gastrointestinal absorption and systemic utilization of nutritional materials in a subject desiring such improvement, comprising administering to said subject a nutritionally effective amount of at least one nutritional material and a potentiating mount of an extract of black pepper, said extract of black pepper having a higher concentration of piperine than natural black pepper* wherein said administering comprises topically applying or parenterally administering to said subject a composition comprising piperine in an amount of from about 0.00004 to about 0.015 mg/kg of body weight of said subject.

26. A method [as recited in claim 24,] *of improving gastrointestinal absorption and systemic utilization of nutritional materials in a subject desiring such improvement, comprising administering to said subject a nutritionally effective amount of at least one nutritional material and a potentiating mount of an extract of black pepper, said extract of black pepper having a higher concentration of piperine than natural black pepper* wherein said administering comprises orally administering to said subject a composition comprising piperine in an amount of from 0.0004 to about 0.15 mg/kg of body weight of said patient.

28. A method [as recited in claim 24,] *of improving gastrointestinal absorption and systemic utilization of nutritional materials in a subject desiring such improvement, comprising administering to said subject a nutritionally effective amount of at least one nutritional material and a potentiating mount of an extract of black pepper, said extract of black pepper having a higher concentration of piperine than natural black pepper* wherein said piperine is administered in an amount in the range of from about 0.00004 to about 0.15 mg per kg of weight of said subject per day.

29. A method [as recited in claim 24] *of improving gastrointestinal absorption and systemic utilization of nutritional materials in a subject desiring such improvement, comprising administering to said subject a nutritionally effective amount of at least one nutritional material and a potentiating mount of an extract of black pepper, said extract of black pepper having a higher concentration of piperine than natural black pepper,* wherein said nutritional material comprises at least one material selected from the group consisitng of herbal extracts, water-soluble vitamins, fat-soluble vitamins, amino acids, minerals and antioxidants.

31. A method of providing an increase in nutrient induced thermogenesis in a subject desiring such an increase, comprising administering to said subject a nutritionally effective amount of a least one nutritional material and a nutrient induced thermogenesis enhancing amount of piperine *in an amount of no more than 15 mg per day, wherein said subject is an adult human.*

33. A method [as recited in claim 31,] *of providing an increase in nutrient induced thermogenesis in a subject desiring such an increase, comprising administering to said subject a nutritionally effective amount of at least one nutritional material and a nutrient induced thermogenesis enhancing amount of piperine* wherein said administering comprises topically applying or parenterally administering to said subject a composition comprising piperine in an amount of from about 0.00004 to about 0.015 mg/kg of body weight of said subject.

34. A method [as recited in claim 31,] *of providing an increase in nutrient induced thermogenesis in a subject desiring such an increase, comprising administering to said subject a nutritionally effective amount of at least one nutritional material and a nutrient induced thermogenesis*

*enhancing amount of piperine* wherein said administering comprises orally administering to said subject a composition comprising piperine in an amount of from 0.0004 to about 0.15 mg/kg of body weight of said patient.

36. A method [as recited in claim 31,] *of providing an increase in nutrient induced thermogenosis in a subject desiring such an increase, comprising administering to said subject a nutritionally effective amount of at least one nutritional material and a nutrient induced thermogenesis enhancing amount of piperine* wherein said piperine is administered in an amount in the range of from about 0.00004 mg to about 0.15 mg per kg of weight of said subject per day.

37. A method [as recited in claim 31,] *of providing an increase in nutrient induced thermogenesis in a subject desiring such an increase, comprising administering to said subject a nutritionally effective amount of at least one nutritional material and a nutrient induced thermogenesis enhancing amount of piperine,* wherein said nutritional material comprises at least one material selected from the group consisting of herbal extracts, water-soluble vitamins, fat-soluble vitamins, amino acids, minerals and antioxidants.

39. A method of providing an increase in nutrient induced thermogenesis in a subject desiring such an increase, comprising administering to said subject a nutritionally effective amount of at least one nutritional material and a potentiating amount of an extract of black pepper *that provides piperine in an amount of no more than 15 mg per day*, said extract of black pepper having a higher concentration of piperine than natural black pepper, *wherein said subject is an adult human.*

40. A method [as recited in claim 39,] *of providing an increase in nutrient induced thermogenesis in a subject desiring such an increase, comprising administering to said subject a nutritionally effective amount of at least one nutritional material and a potentiating amount of an extract of black pepper, said extract of black pepper having a higher concentration of piperine than natural back pepper,* wherein said administering comprises topically applying or parenterally administering to said subject a composition comprising piperine in an amount of from about 0.00004 to about 0.015 mg/kg of body weight of said subject.

41. A method [as recited in claim 39,] *of providing an increase in nutrient induced thermogenesis in a subject desiring such an increase, comprising administering to said subject a nutritionally effective amount of at least one nutritional material and a potentiating amount of an extract of black pepper, said extract of black pepper having a higher concentration of piperine than natural black pepper* wherein said administering comprises orally administering to said subject a composition comprising piperine in an amount of from 0.0004 to about 0.15 mg/kg of body weight of said patient.

43. A method [as recited in claim 39,] *of providing an increase in nutrient induced thermogenesis in a subject desiring such an increase, comprising administering to said subject a nutritionally effective amount of at least one nutritional material and a potentiating amount of an extract of black pepper, said extract of black pepper having a higher concentration of piperine than natural black pepper* wherein said piperine is administered in an amount in the range of from about 0.00004 to about 0.15 mg per kg of weight of said subject per day.

44. A method [as recited in claim 39,] *of providing an increase in nutrient induced thermogenesis in a subject desiring such an increase, comprising administering to said subject a nutritionally effective amount of at least one nutritional material and a potentiating amount of an extract of black pepper, said extract of black pepper having a higher concentration of piperine than natural black pepper,* wherein said nutritional material comprises at least one material selected from the group consisiting of herbal extracts, water-soluble vitamins, fat-soluble vitamins, amino acids, minerals and antioxidants.

46. A method of providing an increase in lean body mass in a subject desiring such an increase, comprising administering to said subject a nutritionally effective amount of at least one nutritional material and a lean body mass enhancing amount of piperine *in an amount of no more than 15 mg per day, wherein said subject is an adult human.*

48. A method [as recited in claim 46,] *of providing an increase in lean body mass in a subject desiring such an increase, comprising administering to said subject a nutritionally effective amount of at least one nutritional material and a lean body mass enhancing amount of piperine* wherein said administering comprises topically applying or parenterally administering to said subject a composition comprising piperine in an amount of from about 0.00004 to about 0.015 mg/kg of body weight of said subject.

49. A method [as recited in claim 46, ] *of providing an increase in lean body mass in a subject desiring such an increase, comprising administering to said subject a nutritionally effective amount of at least one nutritional material and a lean body mass enhancing amount of piperine* wherein said administering comprises orally administering to said subject a composition comprising piperine in an amount of from 0.0004 to about 0.15 mg/kg of body weight of said patient.

51. A method [as recited in claim 46,] *of providing an increase in lean body mass in a subject desiring such an increase, comprising administering to said subject a nutritionally effective amount of a least one nutritional material and a lean body mass enhancing amount of piperine* wherein said piperine is administered in an amount in the range of from about 0.00004 to about 0.15 mg per kg of weight of said subject per day.

52. A method [as recited in claim 46] *of providing an increase in lean body mass in a subject desiring such an increase, comprising administering to said subject a nutritionally effective amount of at least one nutritional material and a lean body mass enhancing amount of piperine,* wherein said nutritional material comprises at least one material selected from the group consisting of herbal extracts, water-soluble vitamins, fat-soluble vitamins, amino acids, minerals and antioxidants.

54. A method of providing an increase in lean body mass in a subject desiring such an increase, comprising administering to said subject a nutritionally effective amount of at least one nutritional material and a potentiating amount of an extract of black pepper *that provides piperine in an amount of no more than 15 mg per day*, said extract of black pepper having a higher concentration of piperine than natural black pepper, *wherein said subject is an adult human.*

55. A method [as recited in claim 54,] *of providing an increase in lean body mass in a subject desiring such an increase, comprising administering to said subject a nutritionally effective amount of at least one nutritional material and a potentiating amount of an extract of black pepper, said extract of black pepper having a higher concentration of piperine than natural black pepper wherein said administering comprises topically applying or parenterally administering to said subject a composition comprising piperine in an amount of from about 0.00004 to about 0.015 mg/kg of body weight of said subject.*

56. A method [as recited in claim 54,] *of providing an increase in lean body mass in a subject desiring such an increase, comprising administering to said subject a nutritionally effective amount of at least one nutritional material and a potentiating amount of an extract of black pepper, said extract of black pepper having a higher concentration of piperine than natural black pepper wherein said administering comprises orally administering to said subject a composition comprising piperine in an amount of from 0.0004 to about 0.15 mg/kg of body weight of said patient.*

58. A method [as recited in claim 54,] *of providing an increase in lean body mass in a subject desiring such an increase, comprising administering to said subject a nutritionally effective amount of at least one nutritional material and a potentiating amount of an extract of black pepper, said extract of black pepper having a higher concentration of piperine than natural black pepper wherein said piperine is administered in an amount in the range of from about 0.00004 to about 0.15 mg per kg of weight of said subject per day.*

59. A method [as recited in claim 54,] *of providing an increase in lean body mass in a subject desiring such an increase, comprising administering to said subject a nutritionally effective amount of at least one nutritional material and a potentiating amount of an extract of black pepper, said extract of black pepper having a higher concentration of piperine than natural black pepper, wherein said nutritional material comprises at least one material selected from the group consisting of herbal extracts, water-soluble vitamins, fat-soluble vitamins, amino acids, minerals and antioxidants.*

*61. A method of increasing nutrient bioavailability in a person desiring such an increase, comprising administering to said person a nutritionally effective amount of at least one nutritional material and a bioavailability enhancing amount of piperine, which bioavailability enhancing amount is no more than 0.15 mg/kg per day.*

*62. A method of increasing nutrient bioavailability in a subject desiring such an increase, comprising administering to said subject a nutritionally effective amount of at least one nutritional material and a potentiating amount of an extract of black pepper, which potentiating amount is no more than 0.15 mg/kg per day, said extract of black pepper having a higher concentration of piperine than natural black pepper.*

*63. A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine, which gastrointestinal absorption and systemic utilization of nutritional materials improving amount is no more than 0.15 mg/kg per day.*

*64. A method of improving gastorintesinal absorption and systemic utilization of nutritional materials in a subject desiring such improvement, comprising administering to said subject a nutritionally effective amount of at least one nutritional material and a potentiating mount of an extract of black pepper which potentiating amount is no more than 0.15 mg/kg per day, said extract of black pepper having a higher concentration of piperine than natural black pepper.*

*65. A method of providing an increase in nutrient induced thermogenesis in a subject desiring such an increase, comprising administering to said subject a nutritionally effective amount of at least one nutritional material and a nutrient induced thermogenesis enhancing amount of piperine, which thermogenesis enhancing amount is no more than 0.15 mg/kg per day.*

*66. A method of providing an increase in nutrient induced thermogenesis in a subject desiring such an increase, comprising administring to said subject a nutritionally effective amount of at least one nutritional matrial and a potentiating amount of an extract of black pepper, which potentiating amount is no more than 0.15 mg/kg per day, said extract of black pepper having a higher concentration of piperine than natural black pepper.*

*67. A method of providing an increase in lean body mass in a subject desiring such an increase, comprising administering to said subject a nutritionally effective amount of at least one nutritional material and a lean body mass enhancing amount of piperine, which lean body mass enhancing amount is no more than 0.15 mg/kg per day.*

*68. A method of providing an increase in lean body mass in a subject desiring such an increase, comprising administering to said subject a nutritionally effective amount of at least one nutritional material and a potentiating amount of an extract of black pepper, which potentiating amount is no more than 0.15 mg/kg per day, said extract of black pepper having a higher concentration of piperine than natural black pepper.*

*69. The method of claim 7, wherein the bioavailability enhancing amount of piperine is from about 0.00004 mg/kg body weight to about 0.15 mg/kg body weight.*

*70. The method of claim 14, wherein the potentiating amount of the extract of black pepper provides piperine in an amount of about 0.00004 mg/kg body weight to about 0.15 mg/kg body weight.*

*71. The method of claim 22, wherein the gastrointestinal absorption and systemic utilization of nutritional materials improving amount of piperine is from about 0.00004 mg/kg body weight to about 0.15 mg/kg body weight.*

*72. The method of claim 29, wherein the potentiating amount of the extract of black pepper provides piperine in an amount of about 0.00004 mg/kg body weight to about 0.15 mg/kg body weight.*

*73. The method of claim 37, wherein the nutrient induced thermogenesis enhancing amount of piperine is from about 0.0004 mg/kg body weight to about 0.15 mg/kg body weight.*

74. The method of claim 44, wherein the protentiating amount of the extract of black pepper provides piperine in an amount of about 0.00004 mg/kg body weight to about 0.15 mg/kg body weight.

75. The method of claim 52, wherein the lean body mass enhancing amount of piperine is from about 0.00004 mg/kg body weight to about 0.15 mg/kg body weight.

76. The method of claim 59, wherein the potentiating amount of the extract of black pepper provides piperine in an amount of about 0.00004 mg/kg body weight to about 0.15 mg/kg body weight.

77. A method of increasing nutrient bioavailability in a subject desiring such an increase, comprising administering to said subject a nutritionally effective amount of at least one nutritional material and a bioavailability enhancing amount of piperine in an amount of from 0.04 mg/kg body weight to 0.25 mg/kg body weight.

78. A method of increasing nutrient bioavailability in a subject desiring such an increase, comprising administering to said subject a nutritionally effective amount of at least one nutritional material and a potentiating amount of an extract of black pepper that provides piperine in an amount of from 0.04 mg/kg body weight to 0.25 mg/kg body weight, said extract of black pepper having a higher concentration of piperine than natural black pepper.

79. A method of improving gastrointestinal absorption and systemic utilization of nutritional materials in a subject desiring such improvement, comprising administering to said subject a nutritionally effective amount of at least one nutritional material and a gastrointestinal absorption and systemic utilization of nutritional materials improving amount of piperine in an amount of from 0.04 mg/kg body weight to 0.25 mg/kg body weight.

80. A method of improving gastrointestinal absorption and systemic utilization of nutritional materials in a subject desiring such improvement, comprising administering to said subject a nutritionally effective amount of at least one nutritional material and a potentiating amount of an extract of black pepper that provides piperine in an amount of from 0.04 mg/kg body weight to 0.25 mg/kg body weight, said extract of black pepper having a higher concentration of piperine than natural black pepper.

81. A method of providing an increase in nutrient induced thermogenesis in a subject desiring such an increase, comprising administering to said subject a nutritionally effective amount of at least one nutritional material and a nutrient induced thermogenesis enhancing amount of piperine in an amount of from 0.04 mg/kg body weight to 0.25 mg/kg body weight.

82. A method of providing an increase in nutrient induced thermogenesis in a subject desiring such an increase, comprising administering to said subject a nutritionally effective amount of at least one nutritional material and a potentiating amount of an extract of black pepper that provides piperine in an amount of from 0.04 mg/kg body weight to 0.25 mg/kg body weight, said extract of black pepper having a higher concentration of piperine than natural black pepper.

83. A method of providing an increase in lean body mass in a subject desiring such an increase, comprising administering to said subject a nutritionally effective amount of at least one nutritional material and a lean body mass enhancing amount of piperine in an amount of from 0.04 mg/kg body weight to 0.25 mg/kg body weight.

84. A method of providing an increase in lean body mass in a subject desiring such an increase, comprising administering to said subject a nutritionally effective amount of at least one nutritional material and a potentiating amount of an extract of black pepper that provides piperine in an amount of from 0.04 mg/kg body weight to 0.25 mg/kg body weight, said extract of black pepper having a higher concentration of piperine than natural black pepper.

85. A method as recited in claim 77, wherein said piperine comprises at least one member selected from the group consisting of synthetically made piperine, extract from black pepper and extract from piper longum.

86. A method as recited in claim 77, wherein said subject is a human.

87. A method as recited in claim 77, wherein said subject is an animal.

88. A method as recited in claim 77, wherein said nutritional material comprises at least one material selected from the group consisting of herbal extracts, water-soluble vitamins, fat-soluble vitamins, amino acids, minerals and antioxidants.

89. A method as recited in claim 88, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

90. A method as recited in claim 78, wherein said subject is a human.

91. A method as recited in claim 78, wherein said subject is an animal.

92. A method as recited in claim 78, wherein said nutritional material comprises at least one material selected from the group consisting of herbal extracts, water-soluble vitamins, fat-soluble vitamins, amino acids, minerals and antioxidants.

93. A method as recited in claim 92, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadiuum, selenium, chromium, iodine, potassium, manganese, copper and magnesium.

94. A method as recited in claim 79, wherein said piperine comprises at least one member selected from the group consisting of synthetically made piperine, extract from black pepper and extract from piper longum.

95. A method as recited in claim 79, wherein said subject is a human.

96. A method as recited in claim 79, wherein said subject is an animal.

97. A method as recited in claim 79, wherein said nutritional material comprises at least one material selected from the group consisting of herbal extracts, water-soluble vitamins, fat-soluble vitamins, amino acids, minerals and antioxidants.

98. A method as recited in claim 97, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

99. A method as recited in claim 80, wherein said subject is a human.

100. A method as recited in claim 80, wherein said subject is an animal.

101. A method as recited in claim 80, wherein said nutritional material comprises at least one material selected from the group consisting of herbal extracts, water-soluble vitamins, fat-soluble vitamins, amino acids, minerals and antioxidants.

102. A method as recited in claim 101, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

103. A method as recited in claim 81, wherein said piperine comprises at least one member selected from the group consisting of synthetically made piperine, extract from black pepper and extract from piper longum.

104. A method as recited in claim 81, wherein said subject is a human.

105. A method as recited in claim 81, wherein said subject is an animal.

106. A method as recited in claim 81, wherein said nutritional material comprises at least one material selected from the group consisitng of herbal extracts, water-soluble vitamins, fat-soluble vitamins, amino acids, minerals and antioxidants.

107. A method as recited in claim 106, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

108. A method as recited in claim 82, wherein said subject is a human.

109. A method as recited in claim 82, wherein said subject is an animal.

110. A method as recited in claim 82, wherein said nutritional material comprises at least one material selected from the group consisting of herbal extracts, water-soluble vitamins, fat-soluble vitamins, amino acids, minerals and antioxidants.

111. A method as recited in claim 110, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

112. A method as recited in claim 83, wherein said piperine comprises at least one member selected from the group consisting of synthetically made piperine, extract from black pepper and extract from piper longum.

113. A method as recited in claim 83, wherein said subject is a human.

114. A method as recited in claim 83, wherein said subject is an animal.

115. A method as recited in claim 83, wherein said nutritional material comprises at least one material selected from the group consisting of herbal extracts, water-soluble vitamins, fat-soluble vitamins, amino acids, minerals and antioxidants.

116. A method as recited in claim 115, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

117. A method as recited in claim 84, wherein said subject is a human.

118. A method as recited in claim 84, wherein said subject is an animal.

119. A method as recited in claim 84, wherein said nutritional material comprises at least one material selected from the group consisting of herbal extracts, water-soluble vitamins, fat-soluble vitamns, amino acids, minerals and antioxidants.

120. A method as recited in claim 119, wherein said herbal extracts are selected from the group consisting of curcumin, boswellin, ashwagandha, ginkgo biloba, capsaicin and aconitine, said water-soluble vitamins are selected from the group consisting of vitamin B1, vitamin B2, niacinamide, vitamin B6, vitamin B12, folic acid and vitamin C, said fat-soluble vitamins are selected from the group consisting of vitamin A, vitamin D, vitamin E and vitamin K, said antioxidants are selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium and zinc, said amino acids are selected from the group consisting of lysine, isoleucine, leucine, threonine, valine, tryptophan, phenylalanine, methionine and L-selenomethionine, and said minerals are selected from the group consisting of calcium, iron, zinc, vanadium, selenium, chromium, iodine, potassium, manganese, copper and magnesium.

* * * * *

(12) EX PARTE REEXAMINATION CERTIFICATE (7703rd)
United States Patent
Majeed et al.

(10) Number: US 5,972,382 C2
(45) Certificate Issued: *Aug. 24, 2010

(54) USE OF PIPERINE AS A BIOAVAILABILITY ENHANCER

(75) Inventors: Muhammed Majeed, Piscataway, NJ (US); Vladimir Badmaev, Piscataway, NJ (US); R. Rajendran, Bangalore (IN)

(73) Assignee: Sabinsa Corporation and Sami Chemical & Extracts (P) Ltd., Bangalore (IN)

Reexamination Request:
No. 90/007,344, Dec. 15, 2004

Reexamination Certificate for:
Patent No.: 5,972,382
Issued: Oct. 26, 1999
Appl. No.: 09/005,594
Filed: Jan. 12, 1998

Reexamination Certificate C1 5,972,382 issued Mar. 4, 2003

(*) Notice: This patent is subject to a terminal disclaimer.

Certificate of Correction issued Dec. 14, 2004.

Certificate of Correction issued Feb. 10, 2004.

Related U.S. Application Data

(60) Division of application No. 08/550,496, filed on Oct. 30, 1995, now Pat. No. 5,744,161, which is a continuation-in-part of application No. 08/393,738, filed on Feb. 24, 1995, now Pat. No. 5,536,506.

(51) Int. Cl.
*A23L 1/221* (2006.01)
*A23L 1/30* (2006.01)
*A61K 47/22* (2006.01)
*C07D 317/60* (2006.01)
*C07D 317/00* (2006.01)

(52) U.S. Cl. .......... 424/464; 424/423; 424/430; 424/434; 424/443; 424/451; 424/734; 424/752; 424/756

(58) Field of Classification Search .......... None
See application file for complete search history.

(56) References Cited

U.S. PATENT DOCUMENTS 5,616,593 A * 4/1997 Patel et al. .......... 514/321

OTHER PUBLICATIONS

1993 Physician' Desk Reference, 47$^{th}$ ed., Roche, Berocca, Berocca Plus, Larobec, pp. 175–756, and 1992, Whitby, Rinsicon, Vicon Forte, pp. 2528–2530.*

Annamalai etal., "Effects of 'Trikatu'and Its Individual Components and Piperine on Gastro Intestinal Tracts: Trikatu—A Bioavailable Enhancer," Indian Drugs 27, Sep. 28, 1989, pp. 595–604.*

* cited by examiner

*Primary Examiner*—Sharon L Turner

(57) ABSTRACT

Compositions and methods for the improvement of gastrointestinal absorption and systemic utilization of nutrients and nutritional supplements, wherein the compositions comprise a minimum of 98% of pure alkaloid piperine. The method comprises oral, topical, or parenteral administration of the compositions of the invention. A new process for the extraction and purification of piperine is also disclosed.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10, 18, 25, 31-34, 36-41, 43-49, 51-56, 58-60, 65-68, 74-76, 81-84 and 103-120 is confirmed.

Claims 5, 12, 20, 27, 35, 42, 50 and 57 were previously cancelled.

Claims 1-2, 4, 6-9, 11, 13-17, 19, 21-24, 26, 28-30, 61-64, 69-72, 77-80 and 85-102 are cancelled.

Claims 3 and 73 are determined to be patentable as amended.

3. A method of increasing nutrient bioavailability in a subject desiring such an increase, comprising administering to said *subject* a nutritionally effective amount of at least one nutritional material and a bioavailability enhancing amount of piperine wherein said administering comprises topically applying or parenterally administering to said subject a composition comprising piperine in an amount of from about 0.00004 to about 0.015 mg/kg of body weight of said subject.

73. The method of claim 37, wherein the nutrient induced thermogenesis enhancing amount of piperine is from about [0.0004] *0.00004* mg/kg body weight to about 0.15 mg/kg body weight.

* * * * *